US012371626B2

(12) United States Patent
Adam et al.

(10) Patent No.: US 12,371,626 B2
(45) Date of Patent: Jul. 29, 2025

(54) PURIFICATION OF WASTE PLASTIC BASED OIL WITH A HIGH TEMPERATURE HYDROPROCESSING

(71) Applicant: TotalEnergies OneTech Belgium, Seneffe (BE)

(72) Inventors: Cindy Adam, Wierde (BE); Delphine Minoux, Nivelles (BE); Walter Vermeiren, Houthalen (BE); Sébastien Leplat, Honfleur (FR); Emmanuel Van Loock, Les Bons Villers (BE); Christophe Breton, Honfleur (FR)

(73) Assignee: TOTALENERGIES ONETECH BELGIUM, Seneffe (BE)

( * ) Notice: Subject to any disclaimer, the term of this patent is extended or adjusted under 35 U.S.C. 154(b) by 377 days.

(21) Appl. No.: 17/917,404

(22) PCT Filed: Apr. 6, 2021

(86) PCT No.: PCT/EP2021/058966
§ 371 (c)(1),
(2) Date: Oct. 6, 2022

(87) PCT Pub. No.: WO2021/204820
PCT Pub. Date: Oct. 14, 2021

(65) Prior Publication Data
US 2023/0287282 A1    Sep. 14, 2023

(30) Foreign Application Priority Data

Apr. 7, 2020  (EP) ..................................... 20168565
Apr. 7, 2020  (EP) ..................................... 20168566
(Continued)

(51) Int. Cl.
*C10G 65/12* (2006.01)
*B01J 20/08* (2006.01)
(Continued)

(52) U.S. Cl.
CPC .............. *C10G 65/12* (2013.01); *B01J 20/08* (2013.01); *B01J 23/755* (2013.01); *B01J 23/883* (2013.01);
(Continued)

(58) Field of Classification Search
CPC .......... C10G 65/12; C10G 1/002; C10G 1/10; C10G 11/18; C10G 31/08; C10G 33/00;
(Continued)

(56) References Cited

U.S. PATENT DOCUMENTS 10,442,997 B2    10/2019  Narayanaswamy et al.
2016/0264874 A1*  9/2016  Narayanaswamy ..... C10G 1/10

FOREIGN PATENT DOCUMENTS

CN    101845323 B    1/2013
CN    103980938 A    8/2014
(Continued)

OTHER PUBLICATIONS

International Search Report of PCT/EP2021/058966 dated Jun. 25, 2021 [PCT/ISA/210].
(Continued)

*Primary Examiner* — Randy Boyer
*Assistant Examiner* — Juan C Valencia
(74) *Attorney, Agent, or Firm* — Sughrue Mion, PLLC

(57) ABSTRACT

A process for the purification of a hydrocarbon stream including: (a) Providing a hydrocarbon stream having a diene value of at least 1.0 and a bromine number of at least 5 gBr2/100g and containing pyrolysis plastic oil; (b) Optionally contact the hydrocarbon stream obtained in step (a) with a silica gel, clays, alkaline or alkaline earth metal oxide, iron oxide, ion exchange resins, active carbon, active aluminum oxide, molecular sieves, alkaline oxide and/or porous supports and silica gel, or any mixture thereof, (c) Heating the stream obtained in step a) or b) followed by a mixing of the
(Continued)

heated stream with a second diluent heated at a temperature of at least 300° C. preferably at least 330° C.; (d) performing an hydroprocessing step at a temperature of at least 250° C. in the presence of H2; and (e) recovering a purified hydrocarbon stream.

19 Claims, 3 Drawing Sheets

(30) Foreign Application Priority Data

| Apr. 7, 2020 | (EP) | .................................... 20168568 |
|---|---|---|
| Apr. 7, 2020 | (EP) | .................................... 20168569 |
| Apr. 7, 2020 | (EP) | .................................... 20168570 |

(51) Int. Cl.

| *B01J 23/755* | (2006.01) |
|---|---|
| *B01J 23/883* | (2006.01) |
| *B01J 35/61* | (2024.01) |
| *C07C 4/04* | (2006.01) |
| *C10G 1/00* | (2006.01) |
| *C10G 1/10* | (2006.01) |
| *C10G 11/18* | (2006.01) |
| *C10G 31/08* | (2006.01) |
| *C10G 33/00* | (2006.01) |
| *C10G 45/08* | (2006.01) |
| *C10G 45/10* | (2006.01) |
| *C10G 45/40* | (2006.01) |
| *C10G 45/44* | (2006.01) |
| *C10G 65/06* | (2006.01) |
| *C10G 67/06* | (2006.01) |
| *C10G 67/14* | (2006.01) |
| *C10G 69/06* | (2006.01) |
| *C10G 69/10* | (2006.01) |

(52) U.S. Cl.
CPC .............. *B01J 35/615* (2024.01); *C07C 4/04* (2013.01); *C10G 1/002* (2013.01); *C10G 1/10* (2013.01); *C10G 11/18* (2013.01); *C10G 31/08* (2013.01); *C10G 33/00* (2013.01); *C10G 45/08* (2013.01); *C10G 45/10* (2013.01); *C10G 45/40* (2013.01); *C10G 45/44* (2013.01); *C10G 65/06* (2013.01); *C10G 67/06* (2013.01); *C10G 67/14* (2013.01); *C10G 69/06* (2013.01); *C10G 69/10* (2013.01); *C10G 2300/1003* (2013.01); *C10G 2300/104* (2013.01); *C10G 2300/201* (2013.01); *C10G 2300/202* (2013.01); *C10G 2300/4006* (2013.01); *C10G 2300/4012* (2013.01); *C10G 2300/4018* (2013.01); *C10G 2300/70* (2013.01); *C10G 2300/807* (2013.01); *C10G 2400/20* (2013.01); *C10G 2400/30* (2013.01)

(58) Field of Classification Search
CPC ........ C10G 45/08; C10G 45/10; C10G 45/40; C10G 45/44; C10G 65/06; C10G 67/06; C10G 67/14; C10G 69/06; C10G 69/10; C10G 2300/1003; C10G 2300/104; C10G 2300/201; C10G 2300/202; C10G 2300/4006; C10G 2300/4012; C10G 2300/4018; C10G 2300/70; C10G 2300/807; C10G 2400/20; C10G 2400/30; C10G 9/36; C10G 21/00; C10G 45/32; C10G 67/04; C10G 47/00; B01J 20/08; B01J 23/755; B01J 23/883; B01J 35/615; C07C 4/04; C10B 53/07; Y02W 30/62
See application file for complete search history.

(56) References Cited

FOREIGN PATENT DOCUMENTS

| CN | 104726134 A | 6/2015 | |
|---|---|---|---|
| JP | 2005-105027 A | 4/2005 | |
| JP | 2007-077324 A | 3/2007 | |
| WO | 2018/055555 A1 | 3/2018 | |
| WO | 2018/127813 A1 | 7/2018 | |
| WO | WO-2020239729 A1 * | 12/2020 | ............. B01D 11/04 |

OTHER PUBLICATIONS

Written Opinion of PCT/EP2021/058966 dated Jun. 25, 2021 [PCT/ISA/237].
Written Opinion of the International Preliminary Examining Authority of PCT/EP2021/058966 dated Feb. 3, 2022 [PCT/IPEA/408].

* cited by examiner

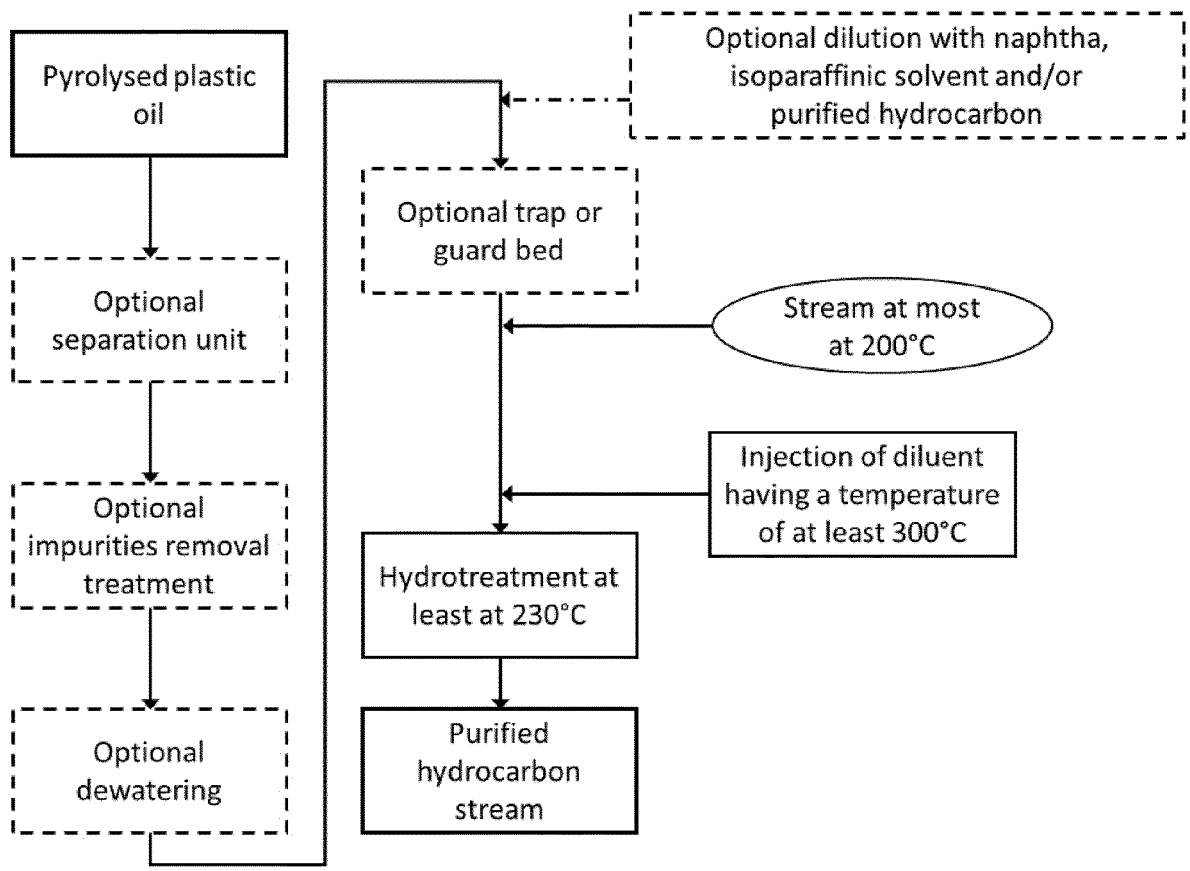
Figure 1. Overview of the possible process stream

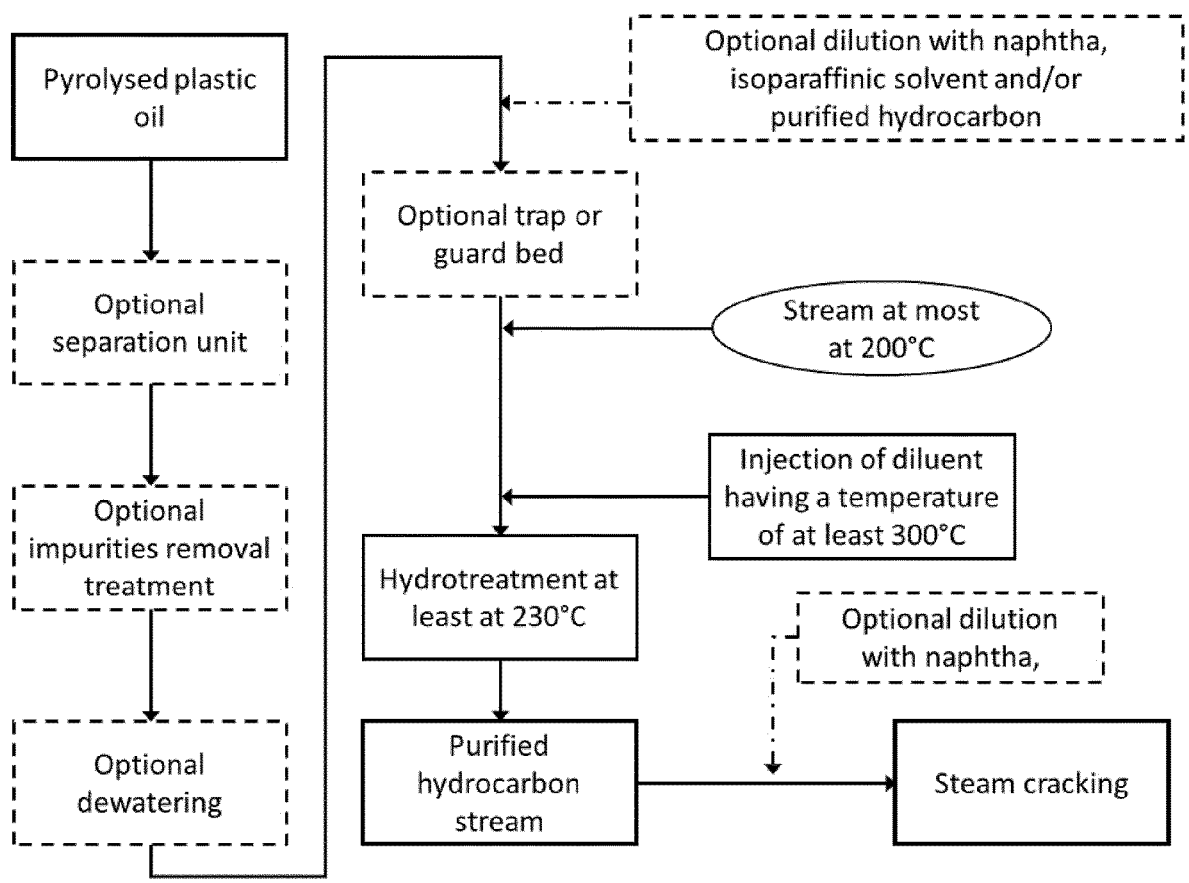
Figure 2. Overview of the possible process stream and application

Figure 3: diene value as funtion of the temperature of the test in the case of example 3.
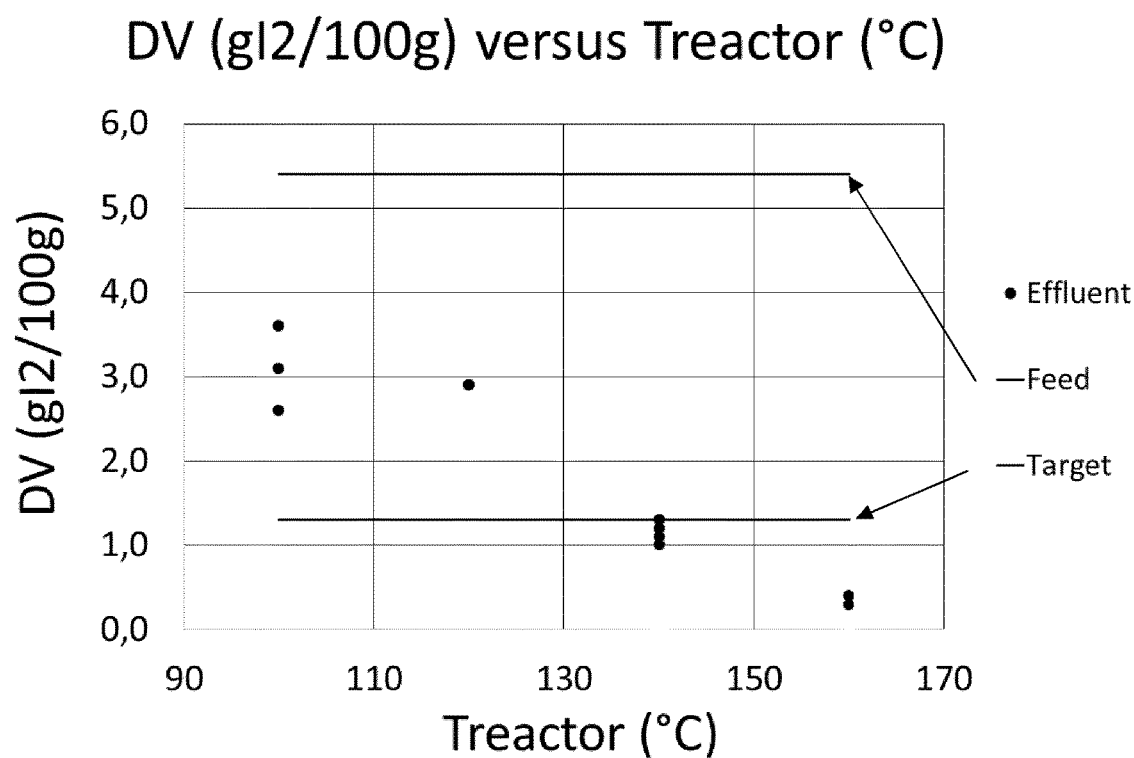

PURIFICATION OF WASTE PLASTIC BASED OIL WITH A HIGH TEMPERATURE HYDROPROCESSING

CROSS REFERENCE TO RELATED APPLICATIONS

This application is a National Stage of International Application No. PCT/EP2021/058966, filed Apr. 6, 2021, claiming priorities to European Patent Application No. 20168568.2, filed Apr. 7, 2020, European Patent Application No. 20168565.8, filed Apr. 7, 2020, European Patent Application No. 20168566.6, filed Apr. 7, 2020, European Patent Application No. 20168569.0, filed Apr. 7, 2020 and European Patent Application No. 20168570.8, filed Apr. 7, 2020.

FIELD OF THE DISCLOSURE

The disclosure relates to the purification and treatment of oil produced from the pyrolysis of waste plastic. In particular, the disclosure relates to the treatments that are performed on the oil obtained from the pyrolysis of plastic in order to be able to further use this oil in other processes such as for example in a steam cracker.

BACKGROUND OF THE DISCLOSURE

Waste plastics are mostly diverted to landfills or are incinerated, with a smaller fraction being diverted to recycling. There is however a strong need, influenced by the regulations to limit waste plastic in landfills. On the other hand, waste plastics disposal into landfills is becoming increasingly difficult. There is therefore a need for recycling waste plastic.

Chemical recycling aims to convert plastic waste into chemicals. It is a process where the chemical structure of the polymer is changed and converted into chemical building blocks including monomers that are then used again as a raw material in chemical processes. There are four methods of chemical recycling, which are substantially different in terms of waste input and obtained products:

Depolymerisation turns mono-stream plastic (only feasible for condensation-type polymers, such as polyesters (notably PET) and polyamides, through hydrolysis or glycolysis) back into monomers or intermediates, which can be re-polymerised into virgin products.

Solvent extraction (dissolution) is used to extract certain polymers using solvents without breaking down the polymer. Any colourants, additives and non-target material are removed by the selective dissolution and the resulting polymer can be reprocessed. Sometimes, it can be used for disassembling multi-layer materials.

Pyrolysis converts mixed plastics into gas, liquid oil and solid residue char. The liquid can be further refined for fuel or new plastics production.

Gasification is able to process unsorted, uncleaned plastic waste and turn it into syngas, which can be used to build liquid intermediates (methanol, ethanol, naphtha, . . . ) feedstocks for making base chemicals as building blocks for new polymers.

The different feedstock recycling methods require each specific feedstock requirements and produce each different product values. Gasification requires least pre-treatment amongst these three methods, followed by pyrolysis methods (thermal and catalytic cracking). Intensive pre-treatment is required in case of depolymerisation.

The low recycling rate stems from the fact that emphasis is mostly on mechanical recycling that is suitable only for homogenous and contaminant free plastic waste, which most of the plastic wastes streams are not. Post-consumers waste, end-of-life vehicles, wastes from construction and demolition, and waste electrical and electronic equipment contain large share of plastics that cannot be recycled via mechanical routes.

Chemical recycling through gasification or pyrolysis still have several hurdles. Firstly, gasification plants are very capital intensive, requires a subsequent syngas conversion unit and hence need to be built at large scale to benefit from economy of scale, which means that large waste streams need to be secured to the plant (implying logistical costs, risk of fluctuating flowrates and varying compositions of the syngas). Pyrolysis can often be justified at smaller scale while the multiple liquid product streams can be further processed in centralized plants. Even though pyrolysis can handle any type of organic material, non-organic materials like metals, glass fibres, halogens, additives and often hetero-atomic containing polymers, like PET and PVC, it remains necessary to remove the impurities from the input stream, ideally before the process or through purification of the pyrolysis oil afterwards.

Pyrolysis and gasification transform plastics, and most of their additives and contaminants into vaporous chemicals while most of the non-volatile contaminants or additives end up in the solid by-product, chars or ashes respectively. In principle, any kind of plastic waste can be converted, although some pre-sorting of non-organic waste is desired and purification of the output material is necessary as some un wanted elements can be present (for instance chlorine, silicon, metals, phosphorous, nitrogen, and other elements.

On the other hand, plastic waste is a complex and heterogeneous material, due to several factors. First, plastic as material refers to numerous different polymers with different chemical properties that need to be separated from each other prior to recycling. The main polymers found in plastic from municipal solid waste are polyethylene terephthalate (PET), polyethylene (PE), polypropylene (PP) and polystyrene (PS). Others are polyurethanes, polyamides (Nylons) and polycarbonates or polyesters.

Second, many different additives are being introduced during the production phase to adjust or improve the properties of the plastic or to fulfil specific requirements. These include additives such as functional additives (stabilisers, antistatic agents, flame retardants, plasticizers, lubricants, slip agents, curing agents, foaming agents, biocides, antioxidants etc.), colourants, fillers, commonly used in plastic packaging as well as additives such as flame retardants, commonly used in plastic for electronics. Additionally, several metal compounds are purposely added during plastic production (often as oxides, acids, etc.). Beside metals other hetero-elements additives are used in making plastics, for instance in flame retardants, plasticisers, stabilisers etc.

Silicon containing organics are used often in plastic formulations. Thanks to their surface characteristics, applications for silicones range from silicone rubbers, used as sealants for joints, to silicone surfactants for cosmetic products while they are increasingly used in the plastics sector, as process enhancing additives (processing aids), and for the modification of polymers.

On top of these hetero-elements, the used waste plastics can have been contaminated during use by sticking residuals of contained liquids (beverages, personal-care products, etc) and of food that can also introduce contamination of the plastic.

Hence it is possible that pyrolyzed plastic oil contains other components such as halogenated compounds, alkali metals, phosphorous compounds, or even iron.

In the particular case of halogenated compounds, halogenate (mainly chlorine —Cl) is mainly coming either from PVC (polyvinylchlorides), or from other plastic additives (entering in the composition of flame retardants or secondary plasticizers for example). The organic chlorides may lead to the formation of HCl in downstream processes, which can cause corrosion of equipment and may also act as a poison for catalysts used in the downstream processes. Ammonium chloride is formed by reaction of HCl with traces of ammonia formed during pyrolysis. At high temperatures, it is not an issue because the ammonium chloride readily dissociates into HCl and NH3 but once temperatures in sections of the plant drops below 100° C., at atmospheric pressure, the compound is stable as NH4Cl and deposits on to equipment.

In the particular case of alkali metals, elements like sodium (Na) can be present. Typical sources of sodium include a malfunctioning washing step, sea water contamination or caustic contamination. Sodium is found in plastic additives (porogen or blowing agents, thermal stabilizers, . . . ) as well. In addition to Na, calcium (Ca) may also be present. Ca can be found in plastic additives (mineral fillers, thermal stabilizers, etc.).

Phosphorus compounds are often found to originate from injection of corrosion inhibitors or flame retardants in the form of thiophosphorus compounds like thiophosphate esters, thiophosphites and tributyl phosphate or organophosphates such as triphenyl phosphate (TPP), resorcinol bis (diphenylphosphate), bisphenol A diphenyl phosphate, and tricresyl phosphate; phosphonates such as dimethyl methylphosphonate; and phosphinates such as aluminium diethyl phosphinate or compounds containing both phosphorus and a halogen. Such compounds include tris(2,3-dibromopropyl) phosphate (brominated tris) and chlorinated organophosphates such as tris(1,3-dichloro-2-propyl)phosphate and tetrakis(2-chlorethyl)dichloroisopentytdiphosphate. Phosphorus compounds are also found as plastics additives as plasticizers.

Iron (Fe) originates from rust and iron scale from corrosion of upstream equipment, as well as from unfiltered particulates present in the feed. In plastics, iron oxides as well as other oxides of metallic salts can be added as insoluble pigments that colour or opacify plastics, or as mineral fillers. Iron carboxylate, like naphthenates can form from corrosion due to organic acids, like terephthalic acids or naphthenic acid in the feed, and the iron readily precipitates out in the presence of heat, water and H2S.

Currently very limited knowledge exists about the fate of metals and other hetero-element containing additives during plastic pyrolysis which are often not analysed in the liquid products. During pyrolysis, the solid plastics goes through a melting phase, decomposition and volatilization. The vapours are condensed forming a liquid product and the gases separated. Some solid residue remains. Hetero-element containing volatiles can end up in the gases (e.g. HCl, NH3 etc) or in the liquid product (chloro-aromatic, bromo-aromatics, phenols, carboxylic aromatics, akyl-amines etc). During pyrolysis at increased temperature, silicones can convert into volatile siloxanes, having boiling points similar to naphtha components.

Finally, pyrolysis of waste plastics allows to produce naphtha, ethylene, propylene and aromatics. But those products are polluted by many hetero elements originating from the waste plastic itself. Significant concentration of silicon and of organic silicon can be found in the pyrolysis plastic oils. Many attempts were focused on the removal of chlorine compounds.

In particular, WO2015/026592 describes a method for processing hydrocarbons wherein a hydrocarbon stream including chlorides from one or more of a crude, vacuum or coker column is contacted with an adsorbent capable of adsorbing the chlorides in an adsorbent bed to provide a dechlorinated hydrocarbon stream to a hydrotreater reactor.

U.S. Pat. No. 6,743,746 (B1) describes a catalyst used in the low-temperature pyrolysis of hydrocarbon-containing polymer materials and being mainly intended for use in the recycling of rubber waste materials. The catalyst is prepared from a carbon-iron component in the form of microscopic carbon particles and ultra-dispersed iron particles.

EP0823469 discloses the pyrolysis of waste plastic including vinyl chlorine in which the dechlorination is firstly performed prior to the pyrolysis process.

WO2014040634 describes plastic wastes which for at least 80 wt-% contain a polymer or a mixture of polymers from a group including polymethyl methacrylate, polypropylene, polyethylene, polystyrene, polyethylene terephthalate and/or polytetrafluoroethylene, are recycled using the following steps: (i) heating the plastic wastes to a temperature at which they are flowable; (ii) pyrolyzing the flowable plastics together with a catalyst and/or an adsorber and withdrawing the resulting gases; (iii) condensing the gases.

US2005165262 describes a low energy method of pyrolysis of rubber or other hydrocarbon material. The hydrocarbon material is heated while maintaining a vacuum, using a clay catalyst.

WO2018025103 describes a process for dechlorination of a hydrocarbon stream comprising the introduction of the hydrocarbon stream together with a first zeolitic catalyst and with a stripping gas to a devolatilization extruder (DE) to produce an extruder effluent. The hydrocarbon stream comprises one or more chloride compounds in an amount of equal to or greater than about 10 ppm chloride, based on the total weight of the hydrocarbon stream and the extruder effluent comprises one or more chloride compounds in an amount of less than the chloride amount in the hydrocarbon stream.

WO2018025104 describes a process for processing mixed plastics comprising simultaneous pyrolysis and dechlorination of the mixed plastics, the process comprising contacting the mixed plastics with a zeolitic catalyst in a pyrolysis unit to produce a hydrocarbon product comprising a gas phase and a liquid phase; and separating the hydrocarbon product into a hydrocarbon gas stream and a hydrocarbon liquid stream, wherein the hydrocarbon gas stream comprises at least a portion of the gas phase of the hydrocarbon product, wherein the hydrocarbon liquid stream comprises at least a portion of the liquid phase of the hydrocarbon product, wherein the hydrocarbon liquid stream comprises one or more chloride compounds in an amount of less than about 100 ppmw chloride, based on the total weight of the hydrocarbon liquid stream, and wherein the hydrocarbon liquid stream is characterized by a viscosity of less than about 400 cP at a temperature of 300° C.

CN 104 726 134 discloses a method for producing high-quality gasoline/diesel from chlorine-containing plastic oil. The method is characterized by comprising the following steps: injecting chlorine-containing plastic oil into a high-temperature dechlorination tower filled with active alumina to perform high-temperature dechlorination, spraying a small amount of NaOH water solution on the top of the high-temperature dechlorination tower, and sending the dechlorinated plastic oil into a catalytic distillation tower filled with a molecular sieve/alumina catalyst to perform reaction and rectification; and pressurizing the plastic oil subjected to catalytic distillation into a hydrofining tower, distilling the hydrofined distillate oil under normal pressure, cutting into gasoline and diesel according to the recovered temperature, and mixing the tower bottom heavy oil and the raw material chlorine-containing plastic oil to react.

CN 103 980 938 discloses a method for producing a clean fuel by adopting chlorine-containing plastic oil. The method is characterized by comprising the steps of injecting the chlorine-containing plastic oil into a catalytic distillation tower filled with a molecular sieve/alumina catalyst for reaction and rectification; performing heat exchange on the chlorine-containing plastic oil after catalytic cracking, feeding the chlorine-containing plastic oil after heat exchange into a low-pressure liquid phase hydrogenation tower, and performing hydrogenation and dechlorination, wherein the used catalyst is a supported metal catalyst; feeding the distillate oil after the liquid phase hydrogenation into a washing tower, circulating the aqueous phase of the lower layer at the tower bottom, compressing the washed distillate oil of the upper layer, feeding the distillate oil into a hydrofining tower, hydrofining with a sulfide catalyst, removing monoene compounds through monoene hydrogenation saturation reaction, removing sulfur, nitrogen and colloids to obtain mixed gasoline and diesel oil without peculiar smell and with high quality, distilling to obtain distillate oil of gasoline and diesel oil, and mixing the heavy oil at the tower bottom and the chlorine-containing plastic oil serving as a raw material for reacting again.

U.S. Pat. No. 10,442,997 discloses methods of reduction of chlorine in pyrolysis products derived from a mixed plastics stream via: (a) causing pyrolysis of a plastic feedstock to produce a first stream of C1-C4 gaseous hydrocarbons and light gas olefins and a second stream comprising the remaining pyrolysis components. The second stream and hydrogen gas may be fed into a hydrocracker to produce a third stream of gaseous C1-C4 hydrocarbon gases and a fourth stream comprising the remaining hydrocracker components. The fourth stream may be fed to either (i) a steam cracker to produce a fifth stream comprising C1-C4 gaseous hydrocarbons and light gas olefins, a sixth stream comprising C6-C8 hydrocarbons and a seventh stream comprising hydrocarbons heavier than C8; or (ii) a fluidized catalytic cracker to produce an eighth stream comprising C1-C4 gases and light gas olefins and a ninth stream comprising hydrocarbons that are C5 or greater.

CN 101 845 323 discloses a process for producing petrol and diesel oil by plastic oil. The plastic oil is used as raw materials to be distilled through catalytic reaction, and then, the hydrogenation refining is carried out for producing high-quality petrol and diesel oil. The process comprises firstly, a step of obtaining petrol and diesel oil distillate from the plastic oil through catalytic reaction distillation; then, selecting the hydrogenation reaction of the petrol and diesel oil distillate under the mild conditions on the metal (noble metal or non-noble metal) catalysts to remove diolefine; next, carrying out hydrogenation refining reaction on the sulphide catalysts; removing monoene compounds through monoene hydrogenation saturation reaction; and carrying out desulfurization, denitrification and colloid removal production to obtain extraneous-odor-free and high-quality petrol and diesel oil.

U.S. Pat. No. 8,911,616 describes an hydrotreating process including providing a first feed stream having a coker naphtha with a bromine number of about 10 to about 120, combining the first feed stream with a second feed stream having a straight run naphtha with a bromine number of less than about 10 to create a combined feed, providing the combined feed to a hydrotreating reactor having at least one catalyst bed, and separating a quench stream from the second feed stream and providing the quench stream after the at least one catalyst bed.

WO 2018/127813 describes a process for producing propylene and cumene comprising converting plastics to hydrocarbon liquid and pyrolysis gas in pyrolyzer; feeding hydrocarbon liquid to hydro processor to yield hydrocarbon product and first gas stream; introducing hydrocarbon product to second separator to produce first C6 aromatics and refined product; feeding refined product to steam cracker to produce steam cracker product; introducing steam cracker product to third separator to produce second C6 aromatics, third propylene stream, second C2-C4 unsaturated stream, C1-4 saturated gas, and balance hydrocarbons product; introducing pyrolysis gas and/or first gas stream to first separator to produce first propylene stream, first C2-C4 unsaturated stream, and saturated gas stream; feeding first and/or second C2-C4 unsaturated stream to metathesis reactor to produce second propylene stream; feeding first and/or second C6 aromatics, and first, second, and/or third propylene stream to alkylation unit to produce cumene; and conveying balance hydrocarbons product to pyrolyzer and/or hydro processor.

JP 2005 105027 describes a method comprising mixing 85% vol. of a straight run naphtha fraction with 15% vol. of plastic cracked oil prepared by cracking a plastic, followed by subjecting the resultant mixture to hydro-refining. In the method, the 97% recovered temperature of straight run naphtha fraction is 110-180° C.; the 97% recovered temperature of the plastic cracked oil is not higher than the sum of the 97% recovered temperature of straight run naphtha fraction and 45° C.; and the end point of the plastic cracking oil is not higher than 200° C.

JP 2007 077324 discloses a method for treating a plastic cracked oil comprises mixing the plastic cracked oil generated by thermal cracking of waste plastic and petroleum fraction and treating the resultant mixture by a petroleum refining process, in which the mixed petroleum stock has a calcium content of 52 mass ppm in terms of the metal.

US2016264874 describes an integrated process for the conversion of waste plastics to high value products. The process allows for operation with a single hydroprocessing reactor which provides simultaneous hydrogenation, dechlorination, and hydrocracking of components of a hydrocarbon stream to specifications which meet steam cracker requirements, with the option to further dechlorinate the treated hydrocarbon stream in a polishing zone.

The above described processes are mainly focused on the removal of chlorine impurities. There are however other impurities in the pyrolysis plastic oil that simply forbid the direct use of pyrolysis plastic oil in other processes like the steam cracker. Indeed, the steam cracker is very sensitive to the presence of olefins or of dienes, of compounds with hetero-atoms and also to the presence of silicon or of organic silicon compounds. There is therefore a need for an improved process for the purification of pyrolysis plastic oil before using it in other process like in steam cracker.

In older documents, like U.S. Pat. Nos. 5,639,937, 5,731,483 and 5,364,995, the pyrolysis of waste plastic followed by the direct use in a steam cracker without any pretreatment before the steam cracker is described. The pyrolysis plastic oil cannot however be used as such. There is clearly a need for a process for purifying the pyrolysis plastic oil before use in a steam cracker. There is especially a need for removing the olefins and dienes, the compounds with hetero-atoms and also impurities (when present) like silicon from pyrolysis plastic oil before the steam cracker.

A common way to convert the unsaturation in hydrocarbon is to perform an hydroprocessing. As the pyrolysis oil is generally rich in olefins, non-conjugated and conjugated diolefins and alkynes, the technical challenge is to find an appropriate way to bring the pyrolysis oil to the required reaction temperature without producing gums or deposits that will foul heat-exchangers and catalytic reactors and providing sufficient hydrogen for the hydrogenation reaction while an efficient heat removal solution to control the temperature rise in the catalytic reactor is necessary. There is therefore a need for an hydroprocessing process enabling the conversion of the unsaturations at a sufficient temperature to have a decent conversion while at the same time avoiding the production of gums or deposits in the various part of the installation.

SUMMARY OF THE DISCLOSURE

The aim of the present disclosure is to provide a purified stream originating from the pyrolysis of plastic wastes. In a preferred embodiment, said stream being further used in steam cracking process in order to produce olefins and aromatics that can be further used to produce plastic.

The disclosure relates to a process for the purification of a hydrocarbon stream comprising the following steps:
  a) Providing a hydrocarbon stream having a diene value of at least 1, preferably 1.5 g I2/100 g as measured according to UOP 326 and a bromine number of at least 5 g Br2/100 g as measured according to ASTM D1159 and containing pyrolysis plastic oil or alternatively providing a hydrocarbon stream containing only pyrolysis plastic oil;
  b) Optionally putting in contact the hydrocarbon stream with silica gel, clays, alkaline or alkaline earth metal oxide, iron oxide, ion exchange resins, active carbon, active aluminium oxide, molecular sieves, alkaline oxide and/or porous supports containing lamellar double hydroxide modified or not and silica gel, or any mixture thereof to trap silicon and/or metals and/or phosphorous and/or halogenates;
  c) Heating the stream obtained at the step a) or b) at a temperature of at most 230° C., preferably at most 200° C., preferably at most 120° C., even more preferably at most 100° C. followed by a mixing of the heated stream with a second diluent having a temperature of at least 250° C. preferably at least 300° C.
  d) performing an hydroprocessing step at a temperature of at least 230° C. preferably 250° C. in the presence of H2,
  e) recovering a purified hydrocarbon stream The present disclosure provides a solution for the heating of the pyrolysis plastic oil containing reactive unsaturated compounds with the help of a second diluent heated at a high temperature. In other words, the heating of the cold reactive pyrolysis oil is performed by mixing it with a hot hydrocarbon stream, the second diluent, hence avoiding contact of the pyrolysis oil with hot surfaces and minimising vaporous phase conditions as much as possible in order to operate the hydroprocessing reaction in substantially liquid conditions.

Pyrolysis plastic oil cannot be directly transformed in steam cracker. Indeed, the presence of unsaturated (olefins, dienes, alkynes etc) in pyrolysis plastic oils would lead among others to problem of fouling at the steam cracker furnaces. A large amount of olefins, alkynes and dienes cannot be sent directly to a steam cracker. Indeed, unsaturated (in particular olefins and even more dienes and alkynes) are coke or deposit precursors. If they are sent to the steam cracker furnace, they will result in the formation of large quantities of coke inducing unwanted stop of the cracker furnace or run length reduction. It is therefore necessary to hydrogenate those olefins, alkynes and dienes before sending the pyrolysis plastic oil to the steam cracker. Hydroprocessing is therefore performed to saturate olefins, alkynes and dienes.

However, it is not easy to hydroprocess pyrolysis plastic oils especially because they contain large quantities of unsaturated compounds. To completely hydroprocess the least reactive olefins, it is necessary to work at a temperature of at least 230° C. or 250° C. But heating pyrolysis plastic oil at such temperature leads to the fouling of the heat exchanger prior to the hydroprocessing unless particularly precautions are taken. This is mainly due to the presence of dienes. It was indeed discovered that it is possible to heat the pyrolysis plastic oils with an overheated diluent. The diluent brings the heat necessary for the reaction and at the same dilutes the stream to avoid thermal runaway in the reactor while bringing more dissolved hydrogen to the hydroprocessing reactor. Fouling in the pre-heater is avoided. This type of heating of the stream allows to perform the hydrogenation of unsaturated in only one hydroprocessing reactor. In other words, it is not necessary to perform a first hydroprocessing followed by a second hydroprocessing. The unsaturated can be directly hydrogenated.

The hydroprocessing also allows to remove the remaining impurities like the metals halogens, oxygen, sulphur or nitrogen-based impurities.

In addition, the pyrolysis plastic oil may contain impurities such as silicon, halogenated compounds, alkali metals, phosphorous compounds, nitrogen or even iron. It has been indeed discovered that it is preferable to remove those impurities before performing the first and/or the second hydrotreating step. When silicon is present in the pyrolysis plastic oil, severe problem is also expected during the second hydrotreating steps. The catalyst operation time will typically depend on the amount of silicon being present in the pyrolysis plastic oil and on silicon "tolerance" of the applied catalyst system. In absence of silicon, a cycle length of more than three years can be reached for the first and/or the second hydrotreating step. Deposition of silicon in form of a silica gel with a partially methylated surface deactivates the catalyst and reduces the typical cycle lengths often to less than one year. The presence of Si has an adverse effect in the subsequent treatment units and poison the catalysts. They also impede regeneration of the contaminated catalysts, by forming a film, of SiO2 on the metallic sites of the catalyst on oxidation of the adsorbed compounds and can hence not be removed by conventional regeneration procedures. It is therefore important to remove the Si before performing the first and/or the second hydrotreating step if Si is present. The presence of halogenate (if any) and more precisely the presence of chlorine leads to corrosion problem associated with HCl and also deposition of NH4Cl. In addition to the problems associated with HCl, any organochlorides tend to cause issues namely catalyst poisoning in the first and/or the second hydrotreating step. For example, catalysts based on nickel, copper and palladium are very susceptible to rapid deactivation by chloride ions. In the case of alkali metals, elements like sodium (Na) may be present. Na is a severe catalyst poison of the catalyst used in the first and/or in the second hydrotreating step. Na can cause significant activity loss even at low levels by promoting sintering of catalytic metals and neutralizing acid sites during the first and/or during the second hydrotreating step. In addition to Na, calcium (Ca) may also be present. Ca is a similar poison to sodium. This type of inorganic alkali or alkaline earth compounds will not easily enter the catalyst's pore system but deposit around the exterior of the catalyst, forming a solid crust between catalyst pellets, which will harm activity and cause pressure drop issues. In the case of phosphorus compounds, they are decomposed in the first and/or in the second hydrotreating step. The phosphates react with the alumina support, forming very stable aluminium phosphates. Accumulated amounts of phosphates will reduce accessibility to the active sites of hydrotreating catalysts and lower the activity accordingly. Iron (Fe) particulates fill the interstitial spaces in the catalyst bed of the first and/or second hydrotreating steps which will result in a higher than expected pressure drop. Apart from Fe, it is also worth noting that the catalyst life of the first and of the second hydrotreating steps are often greatly affected by the content of metals in the pyrolysis plastic oils. Known contaminants, like soluble, dispersed or entrained metals, particulates, and organometallic components or organic metal salts may be present in pyrolysis plastic oils and need to be removed before the first and/or the second hydrotreating step. Deactivation by metals occurs along with the deactivation by coke deposition while metals can also enhance coke formation. Deactivation is ascribed to increasing diffusional resistance caused by accumulation of metals compounds on the pore walls and deposition of metals compounds on the active catalyst phase, e.g. dispersed catalytic metal or metal sulphides.

It was also discovered that the dilution of pyrolysis plastic oil also enables a better control of the exothermicity of the reaction. This is particularly true when the diluent has a broad boiling range. In that case, there is a bigger "thermal wheel" to absorb the exothermicity of the reaction. The diluent helps to adsorb the heat excess of the reaction and hence avoid thermal runaway.

It was also discovered that it is particularly advantaging to have a catalyst in the second hydrotreating step presenting both a hydrotreatment function and a trap function. This is particularly advantaging to trap the Si present in the stream. Indeed, the Si present in the stream may be in the chemical form of siloxane and/or silanol. The siloxanes are decomposed over the hydrotreating function of the catalyst and the product of decomposition are then directly trapped on the catalyst. This allows to completely remove the Si present that would otherwise damage the other process units located downstream.

The described disclosure is also advantaging in that it can be used to stabilize the pyrolysis plastic oil at the exit of the pyrolysis unit. Indeed, the olefins and dienes are very reactive which can result in gum formation. Consequently, the pyrolysis plastic oil is very reactive. It is therefore advantaging to remove the most reactive species before transporting or storing the pyrolysis plastic oil.

The disclosure is further remarkable in that one or more of the following statements is true:

Said pyrolysis plastic oil in said hydrocarbon stream has a starting boiling point of at least 15° C., and a final boiling point of at most 700° C., preferably at most 600° C. even more preferably 560° C., more preferably 450° C. even more preferably 350° C., the most preferred 250° C., and/or said pyrolysis plastic oil has a diene value of at least 1.5, preferably 2, even more preferably 5 g I2/100 g, to at most 50 gI2/100 g as measured according to UOP 326, and/or contains more than 2 ppm wt of metals and/or said pyrolysis plastic oil comprises at least 5 ppm wt of Si to preferably at most 5000 ppm wt, and/or at least 1 ppm wt of Cl to preferably at most 5000 ppm wt, and/or at least 1 ppm wt of P to preferably at most 5000 ppm wt based on the total weight of said pyrolysis plastic oil and/or said hydrocarbon stream contains preferably at least 25 wt %, even more preferably at least 50 wt %, even more preferably at least 75 wt % of said pyrolysis plastic oil and preferably at most 80 wt % of pyrolysis plastic oil, and/or at most 90 wt % preferably at most 95 wt %.

in said hydrocarbon stream at least 10 wt %, preferably 15 wt. %, preferably at least 25 wt. %, even more preferably at least 50 wt. % of said hydrocarbon stream has a boiling point of at least 150° C. based on the total weight of said hydrocarbon stream.

said hydrocarbon stream contains only pyrolysis plastic oil or alternatively said hydrocarbon stream at least 25 wt % preferably at least 50 wt %, even more preferably 75 wt %, even more preferably 90 wt %, of pyrolysis plastic oil the other part of said hydrocarbon stream being a first diluent the weight concentration of said pyrolysis plastic oil in said hydrocarbon stream is chosen so that the total content of olefins, alkynes and diolefins in said hydrocarbon stream at the inlet of the second hydrotreatment step d) is at most 20 wt %, preferably at most 15 wt %, most preferably at most 10 wt % the concentration of said second diluent ranges from 10 wt % to 95 wt % preferably from 20 wt % to 80 wt % even more preferably from 45 wt % to 55 wt % based on the total weight of said second diluent together with said hydrocarbon stream said second diluent is a hydrocarbon stream having a boiling range between 50° C. and 150° C. or a boiling range between 150° C. and 250° C. or a boiling range between 200° C. and 350° C. or Said second diluent contains paraffins with optional addition of a sulfur component, for instance DMDS (dimethyl disulfur), so that the concentration of sulfur is of at least 0.005 wt % of sulfur, preferably 0.05 wt % of sulfur to at most 0.1 wt %

Said second diluent is part of said purified hydrocarbon stream obtained at step e) that is directly recycled at step c) preferably without further heating.

at least 10 wt %, preferably at least 25 wt % even more preferably at least 50 wt % to at most 80 wt % of said purified hydrocarbon stream recovered at step e) is directly recycled at step c) as said second diluent preferably without further heating the step c) is performed at the inlet of the reactor where said hydroprocessing step d) is performed or step c) is performed simultaneously to step d).

the H2 used in step d) is dissolved into said hydrocarbon stream or into said second diluent or into both, preferably with a saturator before being sent to said hydroprocessing step d)

said trap of step b) is a silica gel, activated carbon, activated aluminium oxide and/or molecular sieves working at a temperature ranging from 20 to 100° C. and/or a LHSV between 1 to 10 h-1, and/or a pressure ranging from 1 to 90 barg in presence of H2 or in absence of H2 and/or.

concerning said hydroprocessing step d) one or more of the following statements is true:

After said hydroprocessing step d), the concentration of olefins as measured via the bromine number in said purified hydrocarbon stream is at most 5.0, preferably at most 2.0 gBr2/100 g, more preferably at most 1.5 gBr2/100 g even more preferably at most 0.5 gBr2/100 g as measured according to ASTM D1159. Indeed, the hydroprocessing step e) leads to a reduced concentration of olefins and of diolefins. The purified hydrocarbon stream obtained at step f) can directly be sent at least partially to a steam cracker with a reduced risk of coke formation.

Said hydroprocessing step d) is performed in one or more catalyst beds with preferably an overall temperature increase of at most 150° C., and/or a temperature increase of at most 50° C. over each catalyst bed, even more preferably a temperature increase of 25 to 50 C° over each catalyst bed, the most preferred at temperature increase of 30° C. over each catalyst bed, with preferably intermediary quench between said catalyst beds, said quench being preferably performed with H2 preferably with a bubbler, or a sparge tube, or a perforated annular ring or with said purified hydrocarbon stream recovered at step e)

The inlet temperature is of at least 200° C., preferably 230° C., more preferably 250° C. and at most 500° C.

The LHSV is between 1 to 10 h-1, preferably 2 to 4 h-1 the pressure ranges from 10 to 90 barg in presence of H2

Said hydroprocessing step d) is performed over a catalyst that comprises at least one metal of group VIB as for example Mo, W in combination or not with a promotor selected from at least one metal of group VIII and/or VIIIB as for example Ni and/or Co, and/or mixture thereof, preferably these metals being used in sulfided form and supported on alumina, titania, zirconia, silica, carbon and/or mixtures thereof the ratio H2/hydrocarbon ranges from 200 NL/L to 900 NL/L, preferably in the presence of at least 0.005 wt %, preferably 0.05 wt % even more preferably 0.5 wt % of sulphur, being preferably H2S or organic sulfur compounds, in the stream; and/or on the top of the hydroprocessing step d) a silicon trap is present working at a temperature of at least 230° C., and/or a LHSV between 1 to 10 h-1, and/or a pressure ranging from 10 to 90 barg in presence of H2; optionally with a metal trap working at a temperature of at least 230° C., a LHSV between 1 to 10 h-1, a pressure ranging from 10 to 90 barg in presence of H2

Said hydroprocessing step is performed over at least one catalyst that presents both (i) an hydrotreating function, namely at least one metal of group VIB as for example Mo, W in combination or not with a promotor selected from at least one metal of group VIII and/or VIIIB as for example Ni and/or Co, and/or mixture thereof, preferably these metals being used in sulfided form and (ii) a trap function, namely said catalyst presents a BET surface area ranging from 150 m2/g to 400 m2/g said pyrolysis plastic is originating directly, i.e. without further treatment or modification, from a waste plastic pyrolizer where waste plastic have been thermally pyrolyzed or alternatively said pyrolysis plastic oil and/or said hydrocarbon stream of step a) is treated before said step b) in one or more of the followed pre-treatment unit:

In a desalting unit to remove water-soluble salts

In an impurities removal treatment step to remove silicon, phosphorous, metals and/or halogenated compounds, via preferably a solvent extraction or preferably in a guard bed, said guard bed preferably working at a temperature of at most 200° C., and/or a LHSV between 1 to 10 h-1, and/or a pressure ranging from 1 to 90 barg either in presence of H2 or in the absence of H2

In a separation unit to extract the particles and gums by filtration, centrifugation or a combination of the two technics; and/or In a dewatering unit to remove water in said hydrocarbon stream to reach a water content of less than 0.1% vol preferably of less than 0.05% vol according to ASTM D95.

said purified hydrocarbon stream obtained at step e) is mixed with naphtha, gasoil or crude oil to have a pyrolysis plastic oil concentration from 0.01 wt % to at most 50 wt %; preferably 0.1 wt % to 25 wt % even more preferably 1 wt % to 20 wt % and before being further sent at least partially to a steam cracker to produce olefins, such as ethylene and propylene, and aromatics.

the purified hydrocarbon stream obtained at step e) is sent at least partially and directly to a steam cracker without further dilution and preferably as the only stream sent to the steam cracker, to produce olefins, such as ethylene and propylene, and aromatics the part of said purified hydrocarbon stream obtained at step e), i.e. the effluent of said hydroprocessing step, having an initial boiling point higher than 200° C., preferably higher than 300° C. even more preferably higher than 350° C. is further sent to a FCC, or an hydrocracking unit, or a coker or a visbreaker or blended in crude oil or base oil or crude oil cut to be further refined said process for purification comprises the preliminary step a1) of providing a waste plastic stream; a2) pyrolyzing said waste plastic stream at a temperature of at least 200° C.; a3) recovering a pyrolizer effluent and separating said pyrolizer effluent into a C1 to C4 hydrocarbons fraction, a fraction having a boiling range higher than 350° C. and a fraction being said pyrolysis plastic oil; a4) sending said fraction having a boiling range higher than 350° C. into a FCC, or an hydrocracking unit, a coker or a visbreaker or blending said fraction having a boiling range higher than 350° C. in crude oil or in a crude oil cut to be further refined.

said of pyrolysis plastic oil originates directly from the pyrolysis of plastic wastes without further chemical transformation or separation the effluent obtained after said hydroprocessing step is further washed with water to remove inorganic compounds such as hydrosulphide, hydrogenchloride, ammonia and preferably further hydrocracked at a temperature of 350-430° C., a pressure of 30-180 barg, a LHSV of 0.5-4 h-1, and/or under H2 to hydrocarbons ratio of 800-2000 NL:L to reduce the final boiling point of at least 10% prior to be sent at least partially to the steam cracker said first diluent is selected from a naphtha and/or a paraffinic solvent and/or a diesel or a straight run gasoil, containing at most 1 wt % of sulfur, preferably at most 0.1 wt % of sulfur, and/or an hydrocarbon stream having a boiling range between 50° C. and 150° C. or a boiling range between 150° C. and 250° C. or a boiling range between 200° C. and 350° C. having preferably a bromine number of at most 5 gBr2/100 g, and/or a diene value of at most 0.5 gI2/100 g even more preferably said first diluent is said purified hydrocarbon stream recovered at step e) or any combination thereof.

a guard bed to trap solid particles is located on the top of said hydrotreating before the step c) an optional hydrotreating step b1) is performed at a temperature of at most 225° C. preferably 200° C., remarkable in that one or more of the following statements is true:

The inlet temperature ranges from 25 to 225° C. preferably 200° C.,

The LHSV ranges from 1 to 10 h-1, preferably from 1 to 6 h-1, even more preferably from 2 to 4 h-1, The pressure ranges from 10 to 90 barg, preferably from 15-50 barg or preferably from 25 to 40 barg in presence of H2, and/or the molar ratio of H2 to the total molar sum of alkynes and dienes in said hydrocarbon stream is of at least 1.5, preferably at least 2, most preferably at least 3 to at most 15

Said hydrotreating step b1) is performed in one or more catalyst bed with preferably an overall temperature increase of at most 150° C., more preferably of at most 100° C. and/or a temperature increase of at most 100° C., more preferably of at most 50° C. for each catalyst bed, with preferably intermediary quench between said catalyst beds, said quench being preferably performed with H2 or with said purified hydrocarbon stream recovered at step f)

said step b1) is performed in a fixed bed reactor preferably over a catalyst that comprises at least one metal of group VIII, preferably selected from the group of Pt, Pd, Ni and/or mixture thereof on a support such as alumina, titania, silica, zirconia, magnesia, carbon and/or mixtures thereof; preferably said catalyst is a Ni based catalyst being passivated after its reduction using preferably di-alkyl-sulfide such as DiMethylSulfide (DMS) or DiEthylSulfide (DES) or thiophenic compounds.

said step b1) can also be performed in a fixed bed reactor preferably over a catalyst that comprises at least one metal of group VIB as for example Mo, W in combination or not with a promotor selected from at least one metal of group VIII and/VIIIB as for example Ni and/or Co, and/or mixture thereof, these metals being used in sulfided form and preferably supported on alumina, titania, zirconia, silica, carbon and/or mixtures thereof the effluents obtained at the exit of said hydrotreating step b1) has a diene value of at most 1.5 g I2/100 g, preferably at most 1.0 g I2/100 g even more preferably at most 0.5 g I2/100 g In a preferred embodiment, the disclosure is also advantaging in that part of the purified hydrocarbon stream recovered at step e) can directly be recycled at step c) as the second diluent. In a preferred embodiment, at least 10 wt %, preferably at least 25 wt % even more preferably at least 50 wt % to at most 80 wt % of said purified hydrocarbon stream recovered at step e) is directly recycled at step c) preferably without further heating.

Indeed the hydrogenation of double carbon bonds is a rather exothermic reaction, about 50 to 150 (most typically 50-75 for multi-ring aromatics, 100-110 for single-ring aromatics, 119-126 for mono-olefins or non-conjugated diolefins, 110-115 for conjugated diolefins and 137-148 for alkynes) kJ/mole of consumed hydrogen, that will increase the temperature during the optional hydrotreating or hydrogenation step b1). This leads to a temperature increase of the stream during the passage on the catalyst bed. This heat is advantageously recovered by using said purified hydrocarbon recovered as said second diluent. As such, the heat duty requirements of feed/effluent exchanger are reduced.

In a preferred embodiment, said second diluent or said hydrocarbon stream or both are also used to dissolve at least part of the H2 necessary for the hydroprocessing reaction. It is then possible to incorporate H2 in a liquid. The hydroprocessing reaction can therefore be performed under liquid conditions.

Definitions

For the purpose of the disclosure, the following definitions are given:

The terms "akane" or "alkanes" as used herein describe acyclic branched or unbranched hydrocarbons having the general formula $C_nH_{2n+2}$, and therefore consisting entirely of hydrogen atoms and saturated carbon atoms; see e.g. IUPAC. Compendium of Chemical Terminology, 2nd ed. (1997). The term "alkanes" accordingly describes unbranched alkanes ("normal-paraffins" or "n-paraffins" or "n-alkanes" or "paraffins") and branched alkanes ("iso-paraffins" or "iso-alkanes") but excludes naphthenes (cycloalkanes). They are sometimes referred to by the symbol "HC-".

The terms "olefin" or "alkene" as used herein relate to an unsaturated hydrocarbon compound containing at least one carbon-carbon double bond. They are sometimes referred to by the symbol "HC=".

The terms "alkyne" as used herein relate to an unsaturated hydrocarbon compound containing at least one carbon-carbon triple bond.

The term "hydrocarbon" refers to the alkanes (saturated hydrocarbons), cycloalkanes, aromatics and unsaturated hydrocarbons together.

As used herein, the terms "C#alcohols", "C#alkenes", or "C#hydrocarbons", wherein "#" is a positive integer, is meant to describe respectively all alcohols, alkenes or hydrocarbons having #carbon atoms. Moreover, the term "C#+ alcohols", "C#+ alkenes", or "C#+ hydrocarbons", is meant to describe all alcohol molecules, alkene molecules or hydrocarbons molecules having # or more carbon atoms. Accordingly, the expression "C5+ alcohols" is meant to describe a mixture of alcohols having 5 or more carbon atoms.

Weight hourly space velocity (WHSV) is defined as the hourly weight of flow per unit weight of catalyst and liquid hourly space velocity (LHSV) is defined as the hourly volume of flow per unit of volume of catalyst.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all integer numbers and, where appropriate, fractions subsumed within that range (e.g. 1 to 5 can include 1, 2, 3, 4 when referring to, for example, a number of elements, and can also include 1.5, 2, 2.75 and 3.80, when referring to, for example, measurements). The recitation of endpoints also includes the recited endpoint values themselves (e.g. from 1.0 to 5.0 includes both 1.0 and 5.0). Any numerical range recited herein is intended to include all sub-ranges subsumed therein.

The term "conversion" means the mole fraction (i.e., percent) of a reactant converted to a product or products. The term "selectivity" refers to the percent of converted reactant that went to a specified product.

The terms "wt. %", "vol. %", or "mol. %" refers to a weight, volume, or molar percentage of a component, respectively, based on the total weight, the total volume of material, or total moles, that includes the component. In a non-limiting example, 10 grams of component in 100 grams of the material is 10 wt. % of components.

The term "naphtha" refers to the general definition used in the oil and gas industry. In particular, it refers a hydrocarbon originating from crude oil distillation having a boiling range from 15 to 250° C. as measured by ASTM D2887. Naphtha contains substantially no olefins as the hydrocarbons originates from crude oil. It is generally considered that a naphtha has carbon number between C3 and C11, although the carbon number can reach in some case C15. It is also generally admitted that the density of naphtha ranges from 0.65 to 0.77 g/mL.

The term "pyrolysis plastic oil" refers to the liquid products obtained once waste plastic have been thermally pyrolyzed. The pyrolysis process shall be understood as an unselective thermal cracking process. The pyrolysis involves the breaking of the polymer chains by heating to moderate temperatures (ca. 400-600° C.). Rather than breaking the polymer down to its original monomers, pyrolysis tends to make a range of shorter chain compounds, similar in many ways to the mixtures of hydrocarbons found in crude oil and oil products. A catalyst is sometimes used to reduce the operating temperature. The plastic being pyrolyzed can be of any type. For instance, the plastic being pyrolyzed can be polyethylene, polypropylene, polystyrene, polyesters, polyamides, polycarbonates etc. These pyrolysis plastic oils contain paraffins, i-paraffins (iso-paraffins), dienes, alkynes, olefins, naphthenes, and aromatic components. Pyrolysis plastic oil may also contain impurities such as organic chlorides, organic silicon compounds, metals, salts, sulfur and nitrogen compounds, etc. The origin of the plastic lead to pyrolysis plastic oil is the waste plastic without limitation on the origin or on the nature of the plastic. The composition of the pyrolysis plastic oil is dependent on the type of plastic pyrolyzed. It is however mainly constituted of hydrocarbons having from 1 to 50 carbon atoms and impurities.

The term Diene Value (DV) or Maleic Anhydride Value (MAV) correspond to the amount of maleic anhydride (expressed as equivalents of iodine) which will react with 100 parts of oil under specific conditions. It is a measure of the conjugated double bonds in the oil. One mole of Maleic anhydride corresponds to 1 conjugated double bond. One known method to quantify the diene is the UOP 326: Diene Value by Maleic Anhydride Addition Reaction. The term diene value (DV) refers to the analytical method by titration expressed in g of iodine per 100 g of sample. The term Maleic Anhydride value (MAV) refers to the analytical method by titration expressed in mg of Maleic acid per g of sample. There is a correlation between the MAV=DV*3,863 since 2 moles of iodine correspond to 1 mole of Maleic Anhydride.

The term bromine number corresponds to the amount of bromine in grams reacted by 100 grams of a sample. The number indicates the quantity of olefins in a sample. It is determined in grams of Br2 per 100 grams of solution (gBr2/100 g) and can be measured for instance according to the method ASTM D1159.

The term bromine Index is the number of milligrams of bromine that react with 100 grams of sample. It is determined in milli grams of Br2 per 100 g of solution (mg Br2/100 g) and can be measured for instance according to the method ASTM D2710.

The term boiling point used refers to the boiling point generally used in the oil and gas industry. They are measured at atmospheric pressure. The initial boiling point is defined as the temperature value when the first bubble of vapor is formed. The final boiling point is the highest temperature that can be reached during a standard distillation. At this temperature, no more vapor can be driven over into the condensing units. The determination of the initial and the final boiling point is known per se in the art. Depending on the boiling range of the mixture they can be determine using various standardized methods such as for instance the ASTM D2887 relating to the boiling range distribution of petroleum fractions by gas chromatography. For compositions containing heavier hydrocarbons the ASTM D7169 can alternatively be used. The boiling ranges of the distillates can also advantageously be measure using the ASTM D7500.

The surface area and porous volume are measured via N2 adsorption using usual surface area measurements. In particular, surface area measurements such as "BET" measurement can be used (i.e. ASTM D3663 for the surface area and D4365 for the porous volume). Other techniques well known in the art can also be considered such as mercury adsorption techniques (ASTM D4284). All measurements and data plots as utilized herein were made with a Micromeritics® Tristar 3000@analyser. Surface Area: Total surface area was determined by N2 sorption analysis according to ASTM D 4365-95 (reapproved 2008). Pore diameter and pore volume were determined according to D4641-94 (reapproved 2006).

The concentration of metals in the matrix of hydrocarbon can be determined by any method known in the art. In particular, relevant characterization methods include XRF or ICP-AES methods. The man skilled in the art knows which method is the most adapted to each metal and to which hydrocarbon matrix.

The particular features, structures, characteristics or embodiments may be combined in any suitable manner, as would be apparent to a person skilled in the art from this disclosure, in one or more embodiments.

DESCRIPTION OF THE FIGURES

FIG. 1 describes a simplified overview of a possible process. The pyrolysis plastic oil is firstly distilled in an optional separation unit in order to treat selectively the relevant cut. Then an optional step of removal the impurities is performed. In this step, all type of impurities are removed including salts like NaCl, silicon, phosphorous, metals and/or halogenates. Water is then removed in a dewatering unit. A final optional guard bed is present as a finishing bed to remove the last traces of impurities. The stream is then treated in a via hydroprocessing to remove mainly the diene. The stream is heated before the hydroprocessing with the help of the second diluent. The second diluent brings the heat to the hydroprocessing. An optional dilution of the stream can also be done before the hydroprocessing if necessary.

FIG. 2 describes another possible process very similar to the process of the FIG. 1. This process also differs from the FIG. 1 in that the purified hydrocarbon obtained at the end of the process is directly sent to a steam cracker with an optional dilution with a naphtha.

FIG. 3 diene value represented as function of the reaction temperature in the case of example 3.

DETAILED DESCRIPTION OF THE DISCLOSURE

With regards to the hydrocarbon stream, it can contain a first diluent. In that case, said hydrocarbon stream contains at least 10 wt % of pyrolysis plastic oil. In a preferred embodiment, said hydrocarbon stream presents a bromine number of at most 150 g Br2/100 g, preferably at most 100 g Br2/100 g even more preferably at most 80 g Br2/100 g, the most preferred at most 50 g Br2/100 g as measured according to ASTM D1159. In a preferred embodiment, said hydrocarbon stream contains at least 25 wt % of pyrolysis plastic oil, even more preferably 50 wt % of pyrolysis plastic oil, in the most preferred embodiment at least 75 wt % of pyrolysis plastic oil. It is also possible to use pure pyrolysis plastic oil. In this latter case, the hydrocarbon stream is only pyrolysis plastic oil. The other component of said hydrocarbon stream may include any diluent able to limit the temperature increase at the first and/or second hydroprocessing step. The first and the second diluent can be the same or different. In other words, a diluent shall contain low amount, acceptable by a steam cracker or neither any olefins nor any diene. For instance, part of the purified hydrocarbon stream may be recycled and used as the first or second diluent. A naphtha can also be used as the first or second diluent. The use of naphtha as the first or second diluent is particularly advantaging. Indeed, in a preferred embodiment, the purified hydrocarbon stream is further sent to a steam cracker mixed together with a naphtha. The use of naphtha as the first or second diluent avoids further step of separation of the diluent. The effluent obtained at the end of the inventive process can then preferably be directly sent to the steam cracker. In a preferred embodiment, the pyrolysis plastic oil is diluted into naphtha having a boiling range from 15 to 250° C., preferably 38 to 150° C., as measured with method ASTM D2887 to form the hydrocarbon stream at a concentration of 50 wt %, preferably 75 wt % of pyrolysis plastic oil is diluted in naphtha, even more preferably 90 wt % of pyrolysis plastic oil is diluted in the naphtha.

With regards to the optional dewatering of the hydrocarbon stream, it consists in any method known in the art to remove the water present in a hydrocarbon stream. As non-limiting examples, water can be removed by decantation followed by separation. Water can also be removed in a flash drum. The hydrocarbon stream can alternatively or in addition to the other methods described, can be treated over a desiccant like an alumina or molecular sieve. The various method described above can be used independently or in any combination.

With regards to the optional desalting step, it consists in the desalting techniques known in the art. For instance, typical desalters comprise one or more tanks into which said hydrocarbon stream and water are added. The hydrocarbon stream and water are intensively mixed to enhance the phase interface, typically upstream of the settling tank. The salts from the hydrocarbon stream are extracted via the aqueous phase.

Desalting is a water-washing operation performed because of the negative effect of salts in the downstream processes due to scale formation, corrosion, and catalyst deactivation. These salts can be found in two forms: dissolved in emulsified water droplets in the pyrolysis plastic oil, as a water-in-oil emulsion, or suspended amorphous or crystalline solids. The negative effects of these salts in downstream processes are: salt deposit formation as scales where water is vaporized and corrosion by hydrochloric acid formation from hydrolysis of magnesium and calcium chlorides at high temperatures (about 350° C.) as follows:

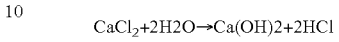

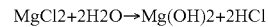

Desalting involves mixing pyrolysis plastic oil and/or said hydrocarbon stream with washing water, using a mixing valve or static mixers to ensure a proper contact between the pyrolysis plastic oil and the water, and then passing it to a separating vessel, where separation between the aqueous and hydrocarbon phases is achieved. Since emulsions can be formed in this process, there is a risk of water carryover in the organic phase. In order to overcome this problem chemical demulsifiers are added to promote the emulsion breaking or an electric field across the settling vessel is applied to coalesce the polar salty water droplets, and, therefore, separation of salty water is achieved.

In order to enhance the effective mixing between the hydrocarbon and aqueous phases and ensure the proper extraction of the salts and minerals into the aqueous phase, a mixing valve is used over which a pressure drop result in shear stress over the droplets that promotes an intimate water and oil contact. In addition to the mixing valve, upstream premixing devices can be used, such as spray nozzles or static mixers. The shear stress needs to be optimized to reach the right balance between smaller droplets, which improves the contact among the phases but however result in more stable emulsion.

Subsequently, the mixture goes to the desalter, a horizontal cylindrical tank that provides long enough residence time to separate the water and oil mixture in two phases. Some water droplets diameters are so small that they do not separate by gravity; so, an electrostatic field between two electrodes installed into the desalter is used to promote coalescence.

When emulsion is too stable and break only slowly, demulsifiers can be used. Demulsifiers are surfactants, when present at low concentration, interacts with the interfaces of the system, altering the interfacial free energies of those interfaces. In particular lipophilic anionic surfactants can be expected in the pyrolysis plastic oil, resulting from the presence of polyesters, polycarbonate and polyamides and from the presence of additives like, antioxidants and UV stabilizers, containing phenols, other oxygenated aromatics and phosphorus containing compounds and slip agents, like fatty acid amides, fatty acid esters, metallic stearates (for example, zinc stearate). An emulsion breaker will lower the interfacial tension and result in coalescence. A hydrophilic demulsifiers will balance the lipophilic surfactant.

In an embodiment, the demulsifying agent can be chosen among water, steam, acids, caustic solutions, complexing agents and their mixtures. Acids are for example strong acids, in particular inorganic acids, such as phosphoric acid, sulphuric acid. Complexing agents are for example weak organic acids (or their corresponding anhydrides) such as acetic acid, citric acid, oxalic acid, tartaric acid, malic acid, maleic acid, fumaric acid, aspartic amino acid, ethylenediaminetetraacetic acid (EDTA). Preferably, the demulsifying agent comprises water, steam, phosphoric acid, acetic acid, citric acid, oxalic acid, tartaric acid, malic acid, fumaric acid, aspartic amino acid, ethylenediaminetetraacetic acid, alkali, salts, chelating agents, crown ethers, or maleic anhydride.

With regards to the traps for silicon and/or metals and/or phosphorous and/or halogenates, it consists in silica gel, clays, alkaline or akaline earth metal oxide, iron oxide, ion exchange resins, active carbon, active aluminium oxide, molecular sieves, and/or porous supports containing lamellar double hydroxide modified or not and silica gel, or any mixture thereof used in the fixed bed techniques known in the art. The trap is able to capture silicon and/or metals and/or phosphorous and/or halogenates, being preferably chosen among Ca Mg Hg via absorption and/or adsorption or it can also be constituted of one or more active guard bed with an adapted porosity. It can work with or without hydrogen coverage. The trap can be constituted of an adsorbent mass such as for instance a hydrated alumina. Molecular sieves can also be used to trap silicon. Other adsorbent can also be used such as silica gel for instance. The silicon trap is preferably able to trap organic silicon. Indeed, it is possible that the silicon present in the streams are in the form of organic silicon.

In a preferred embodiment, silicon and/or metals and/or phosphorous and/or halogenates are trapped with activated carbon. Activated carbon possesses preferably a high surface area (600-1600 m2/g), and is preferably porous and hydrophobic in nature. Those properties lead to a superior adsorption of non-polar molecules or little ionized molecules. Therefore, activated carbon can be used to reduce for instance siloxane from the liquid feed at temperature from 20 to 150° C., at pressures from 1 to 100 bar or from vaporized feed from 150 to 400° C. at pressure from 1 to 100 bar. Regeneration of saturated adsorbent can be performed via heating while using a sweeping gas.

In a preferred embodiment, silicon and/or metals and/or phosphorous and/or halogenates are trapped with silica or silica gel. Silica gel is an amorphous porous material, the molecular formula usually as $(SiO2) \cdot nH2O$, and unlike activated carbon, silica gel possesses polarity, which is more conductive to the adsorption of polar molecules. Because of —Si—O—Si— bonds, siloxanes exhibit partial polar character, which can contribute to adsorb on silica gel surface. The adsorption force of silica gel is often weak enough allowing regeneration of silica gel by heat treatment above 150 up to 300° C. using a sweeping gas.

In a preferred embodiment, silicon and/or metals and/or phosphorous and/or halogenates are trapped with molecular sieves. Molecular sieves are hydrous aluminosilicate substance, with the chemical formula $Na2O \cdot Al2O3 \cdot nSiO2 \cdot xH2O$, which possesses a structure of three-dimensional crystalline regular porous and ionic exchange ability. Compared with silica gel, molecular sieves favour adsorption of high polarity. The regeneration of exhausted absorbents can be achieved via heating at high temperature to remove siloxane. Often, the regeneration is less efficient as the siloxanes might react irreversibly with the molecular sieve. In a most preferred embodiment, the molecular sieves are ion-exchanged or impregnated with a basic element such as Na. Na2O impregnation levels range from 3-10% wt typically and the type of sieve are typically of the A or faujasite crystal structure.

In a preferred embodiment, silicon and/or metals and/or phosphorous and/or halogenates are trapped with activated aluminium oxide. Activated aluminium oxide possesses large surface area (100-600 m2/g), which shows high affinity for siloxanes but also for polar oxide, organic acids, alkaline salts, and water. It can be an alkaline or alkaline-earth or rare-earth containing promoted alumina, the total weight content of these doping elements being less than 20% wt, the doping elements being preferably selected from Na, K, Ca, Mg, La, or mixture thereof. It can also be a metal promoted alumina where the metal is selected from group VI-B metal with hydrogenating activity such as Mo, W and/or from group VIII metal, such as Ni, Fe, Co.

In another embodiment, silicon and/or metals and/or phosphorous and/or halogenates are trapped with alkaline oxide. Alkaline oxide for high temperature treatment such as calcium oxide (CaO) has strong activity to breakdown siloxanes and can be used as non-regeneratable adsorbent at temperature between 15° and 400° C.

In another embodiment, silicon and/or metals and/or phosphorous and/or halogenates are trapped with porous supports containing lamellar double hydroxides, being preferably an hydrotalcite. The hydrotalcite can comprise one or more metals with hydrogenating capacity selected from group VIB or Group VIII, preferably Mo. Those metals can be supported on the surface of the hydrotalcite, or can have been added to the actual structure of the lamellar double hydroxide, in complete or partial substitution; as an example, but without limiting the scope of the present invention, the divalent metal, usually Mg, can be exchanged for Ni, or the trivalent metal, substituted by Fe instead of Al.

The above-mentioned solid adsorbents can be used alone or in any combination in order to optimize the removal of silicon and/or metals and/or phosphorous and/or halogenates.

In another embodiment, silicon and/or metals and/or phosphorous and/or halogenates are trapped with a multi layered guard bed comprising at least two layers wherein the layer on the top of the bed is selected from silica gel, clays, alkaline or alkaline earth metal oxide, iron oxide, ion exchange resins, active carbon, active aluminium oxide, molecular sieves and wherein the layer on the bottom of the bed is selected from silica gel, clays, alkaline or alkaline earth metal oxide, iron oxide, ion exchange resins, active carbon, active aluminium oxide, molecular sieves. More preferably said layer on the top of the guard bed comprises silica gel and/or active carbon and said layer on the bottom of the guard bed comprises molecular sieves and/or active aluminium oxide.

In another embodiment, when the pyrolysis plastic oil contains high quantities of HCl and/or Halogenated compounds (namely at least 500 ppm wt of HCl based on the total amount of pyrolysis plastic oil), particular adsorbents can be used such as silica, clays—such as bentonite, hydrotalcite—alkaline or akaline earth metal oxide—such as iron oxides, copper oxides, zinc oxide, sodium oxide, calcium oxide, magnesium oxide-alumina and alkaline or alkaline-earth promoted alumina-, iron oxide (hematite, magnetite, goethite), ion exchange resins or combination thereof. In a most preferred embodiment, silicon and/or metals and/or phosphorous and/or halogenates containing at least 500 ppm wt of HCl based on the total amount of pyrolysis plastic oil are trapped with activated alumina. As HCl is a polar molecule, it interacts with polar sites on the alumina surface such as hydroxyl groups. The removal mechanism relies predominantly on physical adsorption and low temperature and the high alumina surface area is required to maximize the capacity for HCl removal. The HCl molecules remain physically adsorbed as a surface layer on the alumina and can be removed reversibly by hot purging. Promoted aluminas are a hybrid in which a high alumina surface area has been impregnated with a basic metal oxide or similar salts, often of sodium or calcium. The alumina surface removes HCl through the mechanisms previously described, however the promoter chemically reacts with the HCl giving an additional chloride removal mechanism referred to as chemical absorption. Using sodium oxide as an example of the promoter, the HCl is captured by formation of sodium chloride. This chemical reaction is irreversible unlike physical adsorption and its rate is favoured by higher temperature. The promoted alumina chloride guards are very effective for liquid feeds due to the irreversible nature and high rate of the chemical reaction once the HCl reaches the reactive site.

Another class of chemical absorbents combines Na, Zn and Al oxides in which the first two react with HCl to form complex chloride phases, for example $Na_2ZnCl_4$ and the chemical reactions are irreversible. U.S. Pat. Nos. 4,639,259 and 4,762,537 relate to the use of alumina-based sorbents for removing HCl from gas streams. U.S. Pat. Nos. 5,505,926 and 5,316,998 disclose a promoted alumina sorbent for removing HCl from liquid streams by incorporating an alkali metal oxide such as sodium in excess of 5% by weight on to an activated alumina base. Other Zn-based products range from the mixed metal oxide type composed of ZnO and Na2O and/or CaO. The rate of reaction is improved with an increase in reactor temperature for those basic (mixed) oxides.

With regards to the optional guard bed to trap solid particles Is located on the top of said first hydrotreating step b1), it is placed on the top of said first hydrotreating step b1) to remove the solid particles remaining in the feed such as coke particles coming from heating tubes, iron scales from corrosion, dissolved impurities such as iron, arsenic, calcium-containing compounds, sodium chloride, silicon contained in upstream additives, etc. Grading materials which have high void space to accumulate and 'store' these particulates are frequently used. Effective feed filtration to remove particulates in combination with high void grading provides a longer mitigation of pressure drop buildup. In a preferred embodiment, said guard bed to trap solid particles has a continuously decreasing particle size including a region 25 to 150 centimeters of particles, having a fraction of 0.3 to 2.0 cm diameter range. Since such guard beds to trap solid particles are designed specifically to handle the contaminants, they help to prolong the life of the hydrotreating catalyst and require fewer total catalyst changeouts.

With regards to the impurities removal treatment step to remove silicon, phosphorous, metals and/or halogenate compounds, it consists preferably of a solvent extraction unit. The solvent can be water, alcohol, NaOH, KOH, etc. For example, the silicon extraction with NaOH described in the COMET patent (EP2643432B1), the metals solvent extraction unit used in the refining of used oils.

With regards to the hydroprocessing step d), it consists in a step at a temperature higher than 230° C. preferably higher than 250° C., in presence of hydrogen with well-known catalysts to hydrogenate the olefins and to convert sulfur, nitrogen components into respectively H2S and NH3 and to hydrogenate double carbon bonds. Depending on the composition of the stream entering this second hydroprocessing step, it is either performed in gas phase or the reactor operates in trickle bed mode. This step can have also a metal trap function, a cracking function, a de-aromatization function depending of the characteristic of the catalyst and the used operating condition. This step can be performed in one reactor with different layers of catalysts or several reactors in series depending of the function sought.

In a preferred embodiment, said hydroprocessing step d) is performed over at least one catalyst that presents both (i) an hydrotreating function, and (ii) a trap function. In that case, the preferred operating conditions advantageously be the following: the preferred inlet temperature is of at least 200° C. and at most 500° C.; the preferred LHSV is between 1 to 10 h-1, preferably 2 to 4 h-1; the preferred pressure ranges from 10 to 90 barg in presence of H2; the ratio H2/hydrocarbon ranges from 200 NL/L to 900 NL/L, preferably in the presence of at least 0.005 wt %, preferably 0.05 wt % even more preferably 0.5 wt % of sulphur, being preferably H2S or organic sulfur compounds, in the stream. The use of such catalyst is particularly advantaging because it allows to simultaneously perform the hydrotreating reaction and to trap impurities like silicon that may still be present in the stream.

With regards to the waste plastic pyrolysis, an example of a pyrolysis process for waste plastics is disclosed in U.S. Pat. No. 8,895,790 or in US2014/0228606 and in WO 2016/009333.

In a waste plastic pyrolyzer, mixed plastics (e.g., waste plastics) are placed in pyrolysis unit or pyrolyzer. In the pyrolysis unit, the waste plastic is converted via pyrolysis to a pyrolysis product, wherein the pyrolysis product comprises a gas phase (e.g., pyrolysis gases, such as C1 to C4 gases, hydrogen (H2), carbon monoxide (CO), carbon dioxide (CO2) mainly) and a liquid phase being pyrolysis plastic oil. The plastic waste may include post-consumer waste plastics, such as mixed plastic waste. Mixed plastics can comprise non-chlorinated plastics (e.g., polyolefins, polyethylene, polypropylene, polystyrene, copolymers, etc.), chlorinated plastics (e.g., polyvinyichloride (PVC), polyvinylidene chloride (PVDC), etc.), and the like, or mixtures thereof. Generally, waste plastics comprise long chain molecules or polymer hydrocarbons. Waste plastics may also include used tires.

The pyrolysis unit may be any suitable vessel configured to convert waste plastics into gas phase and liquid phase products (e.g., simultaneously). The vessel may be configured for gas phase, liquid phase, vapor-liquid phase, gas-solid phase, liquid-solid phase, or slurry phase operation. The vessel may contain one or more beds of inert material or pyrolysis catalyst comprising sand, zeolite, alumina, a catalytic cracking catalyst, or combinations thereof. Generally, the pyrolysis catalyst is capable of transferring heat to the components subjected to the pyrolysis process in the pyrolysis unit. Alternatively, the pyrolysis unit can be operated without any catalyst (e.g., pure thermal pyrolysis). The pyrolysis unit may be operated adiabatically, isothermally, nonadiabatically, non-isothermally, or combinations thereof. The pyrolysis reactions of this disclosure may be carried out in a single stage or in multiple stages. For example, the pyrolysis unit can be two reactor vessels fluidly connected in series.

In a configuration where the pyrolysis unit comprises two vessels, the pyrolysis process may be divided into a first stage which is performed in a first vessel and in a second stage fluidly connected downstream of the first stage which is performed in the second vessel. As will be appreciated by one of skill in the art, and with the help of this disclosure, the second stage may enhance the pyrolysis of an intermediate pyrolysis product stream flowing from the first stage into the second stage, to yield a pyrolysis product flowing from the second stage. In some configurations, the first stage may utilize thermal cracking of the waste plastics, and the second stage may utilize thermal or catalytic cracking of the waste plastics to yield the pyrolysis product flowing from the second stage. Alternatively, the first stage may utilize catalytic cracking of the waste plastics, and the second stage may utilize thermal or catalytic cracking of the waste plastics to yield the pyrolysis product flowing from the second stage.

In some configurations, the pyrolysis unit may include one or more equipment configured to convert mixed plastics into gas phase and liquid phase products. The one or more equipment may or may not contain an inert material or pyrolysis catalyst as described above. Examples of such equipment include one or more of heated extruders, heated rotating kiln, heated tank-type reactors, packed bed reactors, bubbling fluidized bed reactors, circulating fluidized bed reactors, empty heated vessels, enclosed heated surfaces where plastic flows down along the wall and cracks, vessels surrounded by ovens or furnaces, or any other suitable equipment offering a heated surface to assist in cracking.

The pyrolysis unit can be configured to pyrolyze (e.g., crack), and in some aspect (e.g., where hydrogen is added to the pyrolysis unit), additionally hydrogenate components of the waste plastic stream fed to the pyrolysis unit. Examples of reactions which may occur in the pyrolysis unit include, but are not limited to isomerization of one or more normal paraffins to one or more i-paraffins, selective ring opening of one or more cycloparaffins to one or more i-paraffins, cracking of long chain length molecules to short chain length molecules, removal of heteroatoms from heteroatom-containing hydrocarbons (e.g., dechlorination), hydrogenation of coke generated in the process, or combinations thereof.

In one or more configurations of the pyrolysis unit, a head space purge gas can be utilized in all or a portion of the pyrolysis stage(s) (conversion of waste plastics to a liquid phase and/or gas phase products) to enhance cracking of plastics, produce valuable products, provide a feed for steam cracking, or combinations thereof. The head space purge gas may include hydrogen (H2), C1 to C4 hydrocarbon gases (e.g., alkanes, methane, ethane, propane, butane, isobutane), inert gases (e.g., nitrogen (N2), argon, helium, steam), and the like, or combinations thereof. The use of a head space purge gas assists in the dechlorination in the pyrolysis unit, when the waste plastic comprises chlorinated plastics. The head space purge gas may be introduced to the pyrolysis unit to aid in the removal of volatiles entrained in the melted mixed plastics present in the pyrolysis unit.

A hydrogen (H2) containing stream can be added to the pyrolysis unit to enrich the pyrolysis unit environment with H2, assist in stripping entrapped hydrogen chloride in the pyrolysis unit, provide a local environment rich in hydrogen in the pyrolysis melt or liquid, or combinations thereof; for example via a H2 containing stream fed directly to the pyrolysis unit independently of the waste plastic stream. In some aspects, H2 can also be introduced along with stream to the pyrolysis unit, with adequate safety measures incorporated for hydrogen handling with plastics feed.

The pyrolysis unit may facilitate any reaction of the components of the waste plastic stream in the presence of, or with, hydrogen. Reactions may occur such as the addition of hydrogen atoms to double bonds of unsaturated molecules (e.g., olefins), resulting in saturated molecules (e.g., paraffins, i-paraffins, naphthenes). Additionally or alternatively, reactions in the pyrolysis unit may cause a rupture of a bond of an organic compound, with a subsequent reaction and/or replacement of a heteroatom with hydrogen.

The use of hydrogen in the pyrolysis unit can have beneficial effects of i) reducing the coke as a result of cracking, ii) keeping the catalyst used (if any) in the process in an active condition, iii) improving removal of chloride from stream such that the pyrolysis product from pyrolysis unit is substantially dechlorinated with respect to waste plastic stream, which minimizes the chloride removal requirement in units downstream of the pyrolysis unit, iv) hydrogenating of olefins, v) reducing diolefins in pyrolysis product, vi) helping operate the pyrolysis unit at reduced temperatures for same levels of conversion of waste plastic stream in the pyrolysis unit, or combinations of i)-vi).

The pyrolysis processes in the pyrolysis unit may be low severity or high severity. Low severity pyrolysis processes may occur at a temperature of less than about 450° C., alternatively 250° C. to 450° C., alternatively 275° C. to 425° C., or alternatively 300° C. to 400° C., and may produce pyrolysis oils rich in mono- and di-olefins as well as a significant amount of aromatics. High severity pyrolysis processes may occur at a temperature of equal to or greater than about 450° C., alternatively 450° C. to 750° C., alternatively 500° C. to 700° C., or alternatively 550° C. to 650° C., and may produce pyrolysis oils rich in aromatics, as well as more gas products (as compared with low severity pyrolysis). As will be appreciated by one of skill in the art, a high severity pyrolysis process will lead to the formation of more olefins and diolefins. Those olefins and diolefins cannot easily be recovered. The hydrotreatment of the present disclosure is therefore required.

A pyrolysis product can be recovered as an effluent from the pyrolysis unit and conveyed (e.g., flowed, for example via pumping, gravity, pressure differential, etc.) to a pyrolysis separating unit. The pyrolysis product can be separated in the pyrolysis separating unit into a pyrolysis gas stream and a pyrolysis plastic oil further used in step a) of the present disclosure. The pyrolysis separating unit may comprise any suitable gas-liquid separator, such as a vapor-liquid separator, oil-gas separators, gas-liquid separators, degassers, deliqulizers, scrubbers, traps, flash drums, compressor suction drums, gravity separators, centrifugal separators, filter vane separators, mist eliminator pads, liquid-gas coalescers, distillation columns, and the like, or combinations thereof.

With regards to the first hydrotreating step b1), it consists mainly in the hydrogenation phase to saturate the conjugated diene and alkynes. Depending on the composition of the hydrocarbon stream, the first step hydrotreating is performed either in liquid phase or in trickle bed mode. This step is well known in steam cracking unit as $1^{st}$ step hydrogenation of pyrolysis gasoline. The first hydrotreating step will hydrogenate the diene and in particularly the conjugated diene and acetylenic bonds. The first hydrotreating step will lead to a decrease the diene value. The decrease of the diene value observed between the inlet and the outlet of the first hydrotreating step should be of at least 10% preferably at least 25% as measured according to UOP 326.

With regards to the steam cracker, it is known per se in the art. The feedstock of the steam cracker in addition to the stream obtained via the inventive process can be ethane, liquefied petroleum gas, naphtha or gasoils. Liquefied petroleum gas (LPG) consists essentially of propane and butanes. Gasoils have a boiling range from about 200 to 350° C., consisting of C10 to C22 hydrocarbons, including essentially linear and branched paraffins, cyclic paraffins and aromatics (including mono-, naphtho- and poly-aromatic).

In particular, the cracking products obtained at the exit of the steam cracker may include ethylene, propylene and benzene, and optionally hydrogen, toluene, xylenes, and 1,3-butadiene.

In a preferred embodiment, the outlet temperature of the steam cracker may range from 800 to 1200° C., preferably from 820 to 1100° C., more preferably from 830 to 950° C., more preferably from 840° C. to 920° C. The outlet temperature may influence the content of high value chemicals in the cracking products produced by the present process.

In a preferred embodiment, the residence time in the steam cracker, through the radiation section of the reactor where the temperature is between 65° and 1200° C., may range from 0.005 to 0.5 seconds, preferably from 0.01 to 0.4 seconds.

In a preferred embodiment, steam cracking is done in presence of steam in a ratio of 0.1 to 1.0 kg steam per kg of hydrocarbon feedstock, preferably from 0.25 to 0.7 kg steam per kg of hydrocarbon feedstock in the steam cracker, preferably in a ratio of 0.35 kg steam per kg of feedstock mixture, to obtain cracking products as defined above.

In a preferred embodiment, the reactor outlet pressure may range from 500 to 1500 mbars, preferably from 700 to 1000 mbars, more preferably may be approx. 850 mbars. The residence time of the feed in the reactor and the temperature are to be considered together. A lower operating pressure results in easier light olefins formation and reduced coke formation. The lowest pressure possible is accomplished by (i) maintaining the output pressure of the reactor as close as possible to atmospheric pressure at the suction of the cracked gas compressor (ii) reducing the pressure of the hydrocarbons by dilution with steam (which has a substantial influence on slowing down coke formation). The steam/feedstock ratio may be maintained at a level sufficient to limit coke formation.

Effluent from the steam cracker contains unreacted feedstock, desired olefins (mainly ethylene and propylene), hydrogen, methane, a mixture of C4's (primarily isobutylene and butadiene), pyrolysis gasoline (aromatics in the C6 to C8 range), ethane, propane, di-olefins (acetylene, methyl acetylene, propadiene), and heavier hydrocarbons that boil in the temperature range of fuel oil (pyrolysis fuel oil). This cracked gas is rapidly quenched to 338-510° C. to stop the pyrolysis reactions, minimize consecutive reactions and to recover the sensible heat in the gas by generating high-pressure steam in parallel transfer-line heat exchangers (TLE's). In gaseous feedstock-based plants, the TLE-quenched gas stream flows forward to a direct water quench tower, where the gas is cooled further with recirculating cold water. In liquid feedstock-based plants, a prefractionator precedes the water quench tower to condense and separate the fuel oil fraction from the cracked gas. In both types of plants, the major portions of the dilution steam and heavy gasoline in the cracked gas are condensed in the water quench tower at 35-40° C. The water-quench gas is subsequently compressed to about 25-35 Bars in 4 or 5 stages. Between compression stages, the condensed water and light gasoline are removed, and the cracked gas is washed with a caustic solution or with a regenerative amine solution, followed by a caustic solution, to remove acid gases (CO2, H2S and SO2). The compressed cracked gas is dried with a desiccant and cooled with propylene and ethylene refrigerants to cryogenic temperatures for the subsequent product fractionation: front-end demethanization, front-end depropanization or front-end deethanization.

The disclosure can be further defined using the following embodiments:

Embodiment 1. Process for the purification of a hydrocarbon stream comprising the following steps:
 a) Providing a hydrocarbon stream having a diene value of at least 1.5 g I2/100 g as measured according to UOP 326 and a bromine number of at least 5 g Br2/100 g as measured according to ASTM D1159 and containing at least 10 wt % of pyrolysis plastic oil preferably 25 wt %, even more preferably 50 wt %, even more preferably 75 wt %, the most preferred 100 wt % the other part of said hydrocarbon stream being a first diluent;
 b) Optionally putting in contact the hydrocarbon stream with a silicon and/or metals and/or phosphorous and/or halogenates trap;
 c) Mixing the stream obtained at the previous step heated at a temperature of at most 200° C., preferably at most 120° C., even more preferably at most 100° C. with a second diluent having a temperature of at least 300° C. preferably at least 330° C.;
 d) performing an hydroprocessing step at a temperature of at least 230° C. preferably 250° C. in the presence of H2;
 e) recovering a purified hydrocarbon stream.

Embodiment 2. Process according to the previous embodiment wherein said pyrolysis plastic oil in said hydrocarbon stream has a starting boiling point of at least 15° C., and a final boiling point of preferably 560° C., more preferably 450° C. even more preferably 350° C., the most preferred 250° C., and/or said pyrolysis plastic oil has a diene value of at least 1.5, preferably 2, even more preferably 5 g I2/100 g, to at most 50 gI2/100 g as measured according to UOP 326, and/or contains more than 2 ppm wt of metals and/or said hydrocarbon stream contains preferably at least 25 wt %, even more preferably at least 50 wt %, even more preferably at least 75 wt % of said pyrolysis plastic oil and preferably at most 80 wt % of pyrolysis plastic oil, and/or at most 90 wt % preferably at most 95 wt %.

Embodiment 3. Process according to any of the preceding embodiments wherein the weight concentration of said pyrolysis plastic oil in said hydrocarbon stream is chosen so that the total content of olefins, alkynes and diolefins in said hydrocarbon stream at the inlet of the second hydrotreatment step d) is at most 20 wt %, preferably at most 15 wt %, most preferably at most 10 wt.

Embodiment 4. Process according to any of the preceding embodiments wherein one or more of the following statements is true:
 the concentration of said second diluent ranges from 10 wt % to 95 wt % preferably from 20 wt % to 80 wt % even more preferably from 45 wt % to 55 wt % based on the total weight of said second diluent together with said hydrocarbon stream;
 Said second diluent has a bromine number of at most 5 gBr2/100 g, and/or a diene value of at most 0.5 gI2/100 g and/or a sulfur content of at most 1000 ppm wt;
 Said second diluent contains paraffins with optional addition of a sulfur component, for instance DMDS, so that the concentration of sulfur is of at least 0.005 wt % of sulfur, preferably 0.05 wt % of sulfur to at most 0.1 wt %;
 Said second diluent is part of said purified hydrocarbon stream obtained at step e) and directly recycled at step c) preferably without further heating; and/or
 at least 10 wt %, preferably at least 25 wt % even more preferably at least 50 wt % to at most 80 wt % of said purified hydrocarbon stream recovered at step e) is directly recycled at step c) as said second diluent preferably without further heating.

Embodiment 5. Process according to any of the preceding embodiments wherein the H2 used in step d) is dissolved into said hydrocarbon stream or into said second diluent or into both, preferably with a saturator before being sent to said hydroprocessing step d).

Embodiment 6. Process according to any of the preceding embodiments wherein said trap of step b) is a silicon trap working at a temperature ranging from 20 to 100° C. and/or a LHSV between 1 to 10 h-1, and/or a pressure ranging from 1 to 90 barg and/or said trap of step d) is a silicon trap working at a temperature of at least 250° C., and/or a LHSV between 1 to 10 h-1, and/or a pressure ranging from 10 to 90 barg in presence of H2.

Embodiment 7. Process accord to any of the preceding embodiments wherein concerning said hydroprocessing step d) one or more of the following statements is true:
- No further hydrogenation step is necessary after said hydroprocessing step d), preferably the concentration of olefins as measured via the bromine number in said purified hydrocarbon stream is at most 5.0, preferably at most 2.0 gBr2/100 g, more preferably at most 1.5 gBr2/100 g even more preferably at most 0.5 gBr2/100 g as measured according to ASTM D1159;
- Said hydroprocessing step d) is performed in one or more catalyst beds with preferably an overall temperature increase of at most 150° C., and/or a temperature increase of at most 50° C. over each catalyst bed, even more preferably a temperature increase of 25 to 50 C° over each catalyst bed, the most preferred a temperature increase of 30° C. over each catalyst bed, with preferably intermediary quench between said catalyst beds, said quench being preferably performed with H2 injected preferably with a bubbler, or a sparge tube, or a perforated annular ring or with said purified hydrocarbon stream recovered at step e);
- The inlet temperature is of at least 230° C. and at most 500° C.;
- The LHSV is between 1 to 10 h-1, preferably 2 to 4 h-1;
- the pressure ranges from 10 to 90 barg in presence of H2;
- Said hydroprocessing step d) is performed over a catalyst that comprises at least one metal of group VIB as for example Mo, W in combination or not with a promotor selected from at least one metal of group VIII and/or VIIIB as for example Ni and/or Co, and/or mixture thereof, preferably these metals being used in sulfided form and supported on alumina, titania, zirconia, silica, carbon and/or mixtures thereof;
- the ratio H2/hydrocarbon ranges from 200 NL/L to 900 NL/L, preferably in the presence of at least 0.005 wt %, preferably 0.05 wt % even more preferably 0.5 wt % of sulphur, being preferably H2S or organic sulfur compounds, in the stream;
- on the top of the hydroprocessing step d) a silicon trap is present working at a temperature of at least 250° C., and/or a LHSV between 1 to 10 h-1, and/or a pressure ranging from 10 to 90 barg in presence of H2; optionally followed by a metal trap working at a temperature of at least 250° C., a LHSV between 1 to 10 h-1, a pressure ranging from 10 to 90 barg in presence of H2; and/or
- the hydroprocessing step d) is performed under liquid conditions.

Embodiment 8. The process according to any of the preceding embodiments wherein said pyrolysis plastic oil and/or said hydrocarbon stream of step a) is treated before said step b) in one or more of the followed pre-treatment unit:
- In a desalting unit to remove water-soluble salts;
- In an impurities removal treatment step to remove silicon, phosphorous, metals and/or halogenated compounds, via preferably a solvent extraction or preferably in a guard bed, said guard bed preferably working at a temperature of at most 250° C., and/or a LHSV between 1 to 10 h-1, and/or a pressure ranging from 1 to 90 barg either in presence of H2 or in the absence of H2 and/or said guard bed is followed by a metal trap working at a temperature of at least 250° C., and/or a LHSV between 1 to 10 h-1, and/or a pressure ranging from 1 to 90 barg in presence of H2;
- In a separation unit to extract the particles and gums by filtration, centrifugation or a combination of the two technics; and/or
- In a dewatering unit to remove water in said hydrocarbon stream to reach a water content of less than 0.1% vol preferably of less than 0.05% vol according to ASTM D95.

Embodiment 9. The process according to any the preceding embodiments wherein said purified hydrocarbon stream obtained at step e) is further mixed with naphtha, gasoil or crude oil to have a pyrolysis plastic oil concentration at the inlet of the steam cracker ranging from 0.01 wt % to at most 50 wt %; preferably 0.1 wt % to 25 wt % even more preferably 1 wt % to 20 wt % and sent to a steam cracker to produce olefins, such as ethylene and propylene, and aromatics.

Embodiment 10. The process according to the embodiments 1 to 8 wherein the purified hydrocarbon stream obtained at step d) is sent directly to the steam cracker without further dilution to produce olefins, such as ethylene and propylene, and aromatics.

Embodiment 11. The process according to any of the preceding embodiments wherein the part of effluent of said hydroprocessing step having an initial boiling point higher than 200° C., preferably higher than 300° C. even more preferably higher than 350° C. is sent to a FCC, or an hydrocracking unit, or a coker or a visbreaker or blended in crude oil or crude oil cut to be further refined.

Embodiment 12. The process according to any of the preceding embodiments wherein said pyrolysis plastic oil of step a) is originating from the stream of pyrolysis waste plastic for which the C1 to C4 hydrocarbons have been removed and/or the components having a boiling point higher than 350° C. have been removed and/or preferably further converted into a FCC, or an hydrocracking unit, a coker or a visbreaker or blended in crude oil or crude oil cut to be further refined.

Embodiment 13. The process according to any of the preceding embodiments wherein the effluent obtained after said hydroprocessing step is further washed with water to remove inorganic compounds such as hydrosulphide, hydrogenchloride, ammonia and preferably further hydrocracked at a temperature of 350-430° C., a pressure of 30-180 barg, a LHSV of 0.5-4 h-1, and/or under H2 to hydrocarbons ratio of 800-2000 NL:L to reduce the final boiling point of at least 10%.

Embodiment 14. The process according to any of the preceding embodiments wherein said first diluent is selected from a naphtha and/or a paraffinic solvent and/or a diesel or a straight run gasoil, containing at most 1 wt % of sulfur, preferably at most 0.1 wt % of sulfur, and/or an hydrocarbon stream having a starting boiling point of at least 15° C., and a final boiling point of preferably 560° C., more preferably 450° C. even more preferably 350° C., the most preferred 250° C., and/or having preferably a bromine number of at most 5 gBr2/100 g, and/or a diene value of at most 0.5 gI2/100 g even more preferably said first diluent is said purified hydrocarbon stream recovered at step e) or any combination thereof.

Embodiment 15. Process according to any of the preceding embodiments wherein before the step c) an optional hydrotreating step b1) is performed of at most 200° C., characterized in that one or more of the following statements is true The inlet temperature ranges from 25 to 200° C.;
The LHSV ranges from 1 to 10 h-1, preferably from 1 to 6 h-1, even more preferably from 2 to 4 h-1;
The pressure ranges from 10 to 90 barg, preferably from 15-50 barg or preferably from 25 to 40 barg in presence of H2, and/or the molar ratio of H2 to the total molar sum of alkynes and dienes in said hydrocarbon stream is of at least 1.5, preferably at least 2, most preferably at least 3 to at most 15;
Said first hydrotreating step is performed in one or more catalyst bed with preferably an overall temperature increase of at most 150° C., more preferably of at most 100° C., and/or a temperature increase of at most 100° C., more preferably of at most 50° C. for each catalyst bed, with preferably intermediary quench between said catalyst beds, said quench being preferably performed with H2 or with said purified hydrocarbon stream recovered at step f);
said first step is performed in a fixed bed reactor preferably over a catalyst that comprises at least one metal of group VIII, preferably selected from the group of Pt, Pd, Ni and/or mixture thereof on a support such as alumina, titania, silica, zirconia, magnesia, carbon; preferably said catalyst is a Ni based catalyst being a passivated after its reduction using preferably di-alkyl-sulfide such as DiMethylSulfide (DMS) or DiEthylSulfide (DES) or thiophenic compounds;
said first step can also be performed in a fixed bed reactor preferably over a catalyst that comprises at least one metal of group VIB as for example Mo, W in combination or not with a promotor selected from at least one metal of group VIII and/VIIIB as for example Ni and/or Co, and/or mixture thereof, these metals being used in sulfided form and preferably supported on alumina, titania, zirconia, silica, carbon and/or mixtures thereof; and/or the effluents obtained at the exit of said first hydrotreating step has a diene value of at most 1.5 g I2/100 g, preferably at most 1.0 g I2/100 g even more preferably at most 0.5 g I2/100 g.

Examples

The embodiments of the present disclosure will be better understood by looking at the different examples below.

Example 1: 2$^{nd}$ Stage Hydroprocessing with Active Guard Bed to Trap Silicon Compound The tests were performed with a sulfided NiMo catalyst by using a mixed feed C6/C7-C9 (60% wt-40% wt) doped with silicon compounds (~10 wppm of hexamethylcyclotrisiloxane (HMCTS) and ~10 wppm of octamethylcyclotetrasiloxane (OMCTS) representative, according to the literature[1], of the decomposition of polysiloxanes. The table below gives more details about the feed used:

|  |  | 60% C6 + 40% C7-C9 (Pygas unit Feed) doped with HMCTS and OMCTS |
|---|---|---|
| Density @15° C. | g/ml | 0.7930 |
| Sulfur content | wppm | <8 |
| Bromine Number | gBr2/100 g | 4.9 |
| C6 Oligomer | wt % | 0.58 |
| Final Boiling Point | ° C. | 231 |
| Si content | HMCTS (ppm) | 11.3 |
|  | OMCTS (ppm) | 11.4 |
| UOP 744 method |  |  |
| Non aromatics | (wt %) | 37.3 |
| Benzene | (wt %) | 27.8 |
| Toluene | (wt %) | 17.7 |
| Ethyl-benzene | (wt %) | 0.7 |
| Xylenes o-m-p | (wt %) | 1.9 |
| Other aromatics | (wt %) | 10.2 |

The tests were performed at two temperatures 245° C. and 290° C. and two LHSV. The different operating conditions are summarized in Table 2.

| Condition | Pressure (bars) | LHSV (h$^{-1}$) | T (° C.) | H$_2$/HC (Nl/l) | Liquid flow (ml/h) | Gas flow (Nl/h) | Days |
|---|---|---|---|---|---|---|---|
| 1 | 27.7 | 1.1 | 245 | 290 | 110 | 31.9 | 6 |
| 2 |  |  | 290 |  |  |  | 6 |
| 3 |  | 10 |  |  | 1000 | 31.9 | 3 |

The table here below shows the organic silicon content in the feed and in the effluents for the different conditions.

| Pollutants ppm | HMCTS 11.3 ppm | OMCTS 11.4 ppm | Si by XRF 9.8 ppm | Br number/index 4.9 gBr2/100 g |
|---|---|---|---|---|
| T (° C.) 245 | <200 ppb. | <200 ppb | <1 ppm | <50 mgBr2/100 g |
| 290 LHSV = 1.1 h$^{-1}$ | <200 ppb | <200 ppb | <1 ppm | <50 mgBr2/100 g |
| LHSV = 10 h$^{-1}$ | <200 ppb | <200 ppb | <1 ppp | <50 mgBr2/100 g |

In terms of Si capture, the trap is convenient and efficient, even at higher LHSV.

Example 2: 2$^{nd}$ Stage Hydrotreating with Active Guard Bed to Trap Silicon Compound and Hydrogenate The tests were performed on a pyrolysis oil with a sulfided NiMo catalyst in the following conditions.

| Pressure (barg) | 27.7 |
|---|---|
| LHSV (h$^{-1}$) | 1.1 |
| Feed Flowrate (ml/h) | 55 |
| H$_2$/HC (Nl/l) | 290 |
| H2 flowrate (Nl/h) | 16 |
| Temperature (° C.) | Start Of Run: 245° C. The temperature was then gradually increased |

The Pyrolysis oil was diluted in an inert product (Isoparaffinic cut) and characterized.

| Feed | FEED-50% |
|---|---|
| IBP-FBP (° C.) | 83-427 |
| MV15 (g/ml) | 0.7806 |
| S by UV (ppm) | 6.2 |
| N (ppm) | 103.5 |
| Chlorine (ppm) | 44 |
| Metals par ICP-AES (ppm) | Fe: 4, K: 1 |
| Si by XRF (ppm) | 35 |
| Br Number_ (gBr/100 g) | 33 |
| Diene Value (gI2/100 g) | 1.7 |

The table here below show the results on this catalyst which is able to hydrogenate the double bonds and capture the silicon.

| | H2 = 16 NI/h | HC = 43 g/h | | |
|---|---|---|---|---|
| T (° C.) | Br Number (gBr2/100 g) | Abattement | Si_XRF (ppm) | Abattement |
| FEED3-100 | 33 (±3) | ER 10% | 35 (±3) | ER 10% |
| 245° C. | 7.2 | 78% | 2 | 94% |
| 255° C. | 6.6 | 80% | 3 | 91% |
| 265° C. | 5.9 | 82% | 1 | 97% |
| 275° C. | 6.4 | 81% | 1 | 97% |
| 285° C. | 7.0 | 79% | 1 | 97% |
| 290° C. | 8.9 | 73% | 1 | 97% |

On the effluent at 255° C., a molecular siloxane speciation was realized by GC-MS-SIM which highlight the abatements of siloxane molecules.

| | FEED-50% | Effluent at 255° C. |
|---|---|---|
| Si par XRF (ppm) | 35 | 3 |
| Spéciation siloxane | (ppm) | (ppm) |
| Hexamethylcyclotrisiloxane | 16.5 | < |
| Octamethylcyclotetrasiloxane | 10.5 | < |
| Decamethylcyclopentasiloxane | 3.5 | < |
| Dodecamethylcyclohexasiloxane | 2 | < |
| Hexamethyldisiloxane | < | < |
| Octamethyltrisiloxane | < | < |
| Decamethyltetrasiloxane | < | < |
| Dodecamethylpentasiloxane | < | < |
| Somme (ppmSi) | 32.5 | <1 |

This example shows that a NiMo catalyst is able to both hydrogenate the olefins and at the same time trapping the siloxanes.

Example 2: Liquid Phase First Stage Hydroprocessing

The tests were performed using a pyrolysis plastic oil cut having a boiling point ranging from 70° C. to 460° C., a DV of about 4 g I2/100 g, a nitrogen content of about 210 wtppm and a sulfur content of about 20 ppm. A Ni on alumina catalyst was used in dilution 1:2 with silicon carbide 0.21 mm as diluent (50 ml of catalyst for 100 ml of SiC). The Nickel catalyst was dried under nitrogen (50 Nl/h) at 180° C. and reduced under hydrogen (minimum 20 Nl/h) at about 400° C. during min 15 h; then the temperature was reduced till 180° C. and the hydrogen was replaced by nitrogen to purge the reactor. Finally, the temperature was reduced to 50° C. and a paraffinic feed was injected to stabilize the catalyst.

The pyrolysis plastic oil cut was used pure.

The test was performed in the following operating conditions.

| Pression (barg) | 30 |
|---|---|
| LHSV ($h^{-1}$) | 2 |
| Q liquid (ml/h) | 100 |
| Q_H2 (NI/h) | 3 moles of hydrogen per mole of dienes. |
| Temperature (° C.) | Start Of Run: 50° |

The temperature was increased till having the lowest DV in the liquid effluent. The Bromine number (BrN) is mentioned for information and to highlight that not all the olefins have been hydrogenated in these conditions.

| | DV(gI2/100 g) | BrN(gBr2/100 g) | Si by XRF (ppm) |
|---|---|---|---|
| Feed | 4.1 ((±0.5) | 60.1 (±6) | 71 (±7) |
| Tinlet (° C.) | Effluent | Effluent | Effluent |
| 50 | 1.9 | 46.3 | — |
| 60 | 1.8 | 54.9 | — |
| 90 | 0.1 | 47.2 | 75 |

No noticeable exotherm was observed during the test, whatever the inlet Temperature considered. Increasing the temperature up to 120° C., allowed to decrease the Bromine number down to 42 gBr2/100 g. This example demonstrates that it is possible to hydrogenate the diolefins to a high extent while conserving the olefins of a pyrolysis plastic oil while maintaining the exothermicity in the catalyst bed at an acceptable level. The example demonstrates also that the silicon compound passes through this first hydrotreatment step.

Example 3

Liquid Phase First Stage Hydroprocessing

The tests were performed using a pyrolysis oil cut having a boiling point ranging from 20 to 250° C., a MAV of about 32. A sulfided NiMo on alumina catalyst was used in dilution with silicon carbide at equal volumes.

The pyrolysis oil cut was diluted with a paraffinic diluent to have a MAV at the inlet of about 21 mg anhydride maleic/g (or a DV of about 5,4 gI2/100 g).

The test was performed in the following operating conditions.

| Pression (barg) | 25 |
|---|---|
| LHSV ($h^{-1}$) | 2 |
| liquide flow rate (ml/h) | 200 |
| $H_2$/HC (NI/l) | 7 |
| H2 flow rate (NI/h) | 1.4 |
| Inlet Temperature (° C.) | Start Of Run: 50° |

No noticeable exotherm was observed during the test, whatever the inlet Temperature considered. The temperature was increased till having a MAV under 5.4 mg anhydride maleic/g (or a DV under 1,3 gI2/100 g) in the liquid effluent. This example demonstrates that it is possible to hydrogenate the diolefins and the olefins of a pyrolysis plastic oil while maintaining the exothermicity in the catalyst bed at an acceptable level.

Example 5: Adsorbents Used in Fixed Bed Reactor

It is foreseen that adsorbents will behave as it is presented in the results below. The tests were performed using a pyrolysis plastic oil cut having a boiling point ranging from 40° C. to 350° C. The water is expected to be below 100 ppm weight. The chlorine content of is expected to be in the range of about 200 ppm, the silicon content is expected to be in the range of about 100 ppm. The oxygen content of is expected in the range of about 1.0 wt %. The nitrogen is probably less than 2000 ppm wt. The adsorbent is chosen as being a promoted alumina (or active aluminium oxide) of spherical shape with 3.0 mm mean diameter with a surface area of 220 m2/g and a density of 0.75 kg/L. The adsorbent is disposed in a fixed bed under a continuous flow. Before the test the adsorbent shall be dried under nitrogen in up flow mode. The pyrolysis plastic oil shall be injected up flow. Dilution of the pyrolysis plastic oil with a first diluent can be done prior to the adsorption over the adsorbent. Alternatively, the pyrolysis plastic oil can be passed through the adsorbent without being diluted. This latter option was estimated in this example. The pyrolysis oil was injected in up flow mode at 20° C. under nitrogen blanketing.

|  |  | Pyrolysis Oil |
|---|---|---|
| Density @15° C. | g/mL | 0.80 |
| Silicon | ppm | 100 |
| Oxygen | wt % | 1.0 |
| Chlorine | ppm | 200 |
| Nitrogen | ppm | 2000 |

The tests were performed at ambient temperature (20° C.) and at three LHSV. The different operating conditions and performances expected are summarized in the following table, wherein weight percentage is given as the removed proportion of each measured element after treatment relative to the proportion of said element in the feedstock (here: plastic pyrolysis oil) before treatment. For sake of clarity, "100 wt %" means that the entirety of the component of interest has been removed:

| Condition | Pressure (barg) | LHSV (h$^{-1}$) | T (° C.) | Oxygen wt % | Chlorine wt % | Silicon wt % | Nitrogen wt % |
|---|---|---|---|---|---|---|---|
| 1 | 1 | 0.5 | 20 | 30 | 15 | 5 | 18 |
| 2 | 1 | 1 | 20 | 28 | 12 | 2 | 12 |
| 3 | 1 | 2 | 20 | 23 | 10 | n.s. | 9 |

*n.s. = not significant;

Impurities measurement was done at start of run. The overall oxygen uptake by the adsorbent is ranging from 2 to 15 wt % depending on operating conditions especially LHSV and the physical-chemical properties and nature of adsorbent used. This overall uptake corresponds to the maximal amount of oxygen containing impurities which can be trapped within the said adsorbent.

Very similar results can be obtained with silica gel having a spherical diameter of 5 mm, a surface area of about 500 m2/g, a density of 600 kg/m3 and a pore volume of about 0.42 cm3/g. The expected results with the same operating conditions are presented below

| Condition | Pressure (barg) | LHSV (h$^{-1}$) | T (° C.) | Oxygen wt % | Chlorine wt % | Silicon wt % | Nitrogen wt % |
|---|---|---|---|---|---|---|---|
| 1 | 1 | 0.5 | 20 | 20 | 12 | 7 | 30 |
| 2 | 1 | 1 | 20 | 15 | 9 | 5 | 22 |
| 3 | 1 | 2 | 20 | 11 | 7 | n.s. | 416 |

*n.s. = not significant;

It appears from the examples described above that the promoted alumina and silica gel should allow to trap oxygen, chlorine, nitrogen and also silicon to a certain extend too.

The invention claimed is:

1. A method for the purification of a hydrocarbon stream comprising the following steps:
    a) providing a hydrocarbon stream having a diene value of at least 1.0 g I2/100 g as measured according to UOP 326 and a bromine number of at least 5 g Br2/100 g as measured according to ASTM D 1159 and containing pyrolysis plastic oil, the other part of said hydrocarbon stream being a first diluent or alternatively providing a hydrocarbon stream containing only pyrolysis plastic oil;
    b) optionally putting in contact the hydrocarbon stream with silica gel, clays, alkaline or alkaline earth metal oxide, iron oxide, ion exchange resins, active carbon, active aluminium oxide, molecular sieves, alkaline oxide and/or porous supports containing lamellar double hydroxide modified or not and silica gel, or any mixture thereof to trap silicon and/or metals and/or phosphorous and/or halogenates;
    c) heating the stream obtained at the step a) or b) at a temperature of at most 230° C., followed by a mixing of the heated stream with a second diluent having a temperature of at least 250° C.;
    d) performing an hydroprocessing step at a temperature of at least 230° C. in the presence of H2 on the mixed stream of step c);
    e) recovering a purified hydrocarbon stream from the hydroprocessing step,
    wherein said second diluent is part of said purified hydrocarbon stream obtained at step e) that is directly recycled at step c), and
    said purified hydrocarbon stream obtained at step e) is mixed with naphtha, gasoil or crude oil to have a pyrolysis plastic oil concentration ranging from 0.01 wt % to at most 50 wt %; and before being further sent at least partially to a steam cracker to produce olefins and aromatics.

2. The method according to claim 1, wherein said pyrolysis plastic oil in said hydrocarbon stream has a starting boiling point of at least 15° C., and a final boiling point of at most 700° C., and/or said hydrocarbon stream contains at least 25 wt % of said pyrolysis plastic oil and at most 80 wt % of pyrolysis plastic oil, and/or at most 90 wt % of the other part of said hydrocarbon stream being a first diluent and/or said pyrolysis plastic oil has a diene value of at least 1.5 g I2/100 g, to at most 50 gI2/100 g as measured according to UOP 326, and/or contains more than 2 ppm wt of metals and/or said pyrolysis plastic oil comprises at least 5 ppm wt of Si to at most 5000 ppm wt, and/or at least 1 ppm wt of Cl to at most 5000 ppm wt, and/or at least 1 ppm wt of P to at most 5000 ppm wt based on the total weight of said pyrolysis plastic oil.

3. The method according to claim 1, wherein said hydrocarbon stream contains at least 25 wt % of pyrolysis plastic oil, the other part of said hydrocarbon stream being a first diluent.

4. The method according to claim 1, wherein one or more of the following statements is true:
    the concentration of said second diluent ranges from 10 wt % to 95 wt % based on the total weight of said second diluent together with said hydrocarbon stream;

Said second diluent has a bromine number of at most 5 gBr2/100 g, and/or a diene value of at most 0.5 gI2/100 g and/or a sulfur content of at most 1000 ppm wt;

Said second diluent contains paraffins with optional addition of a sulfur component, so that the concentration of sulfur is of at least 0.005 wt % of sulfur to at most 0.1 wt % in the stream entering in said second hydrotreating step;

at least 10 wt % to at most 80 wt % of said purified hydrocarbon stream recovered at step e) is directly recycled at step c) as said second diluent;

the step c) is performed at the inlet of the reactor where said hydroprocessing step d) is performed or step c) is performed simultaneously to step d).

5. The method according to claim 1, wherein the H2 used in step d) is dissolved into said hydrocarbon stream or into said second diluent or into both before being sent to said hydroprocessing step d).

6. The method according to claim 1, wherein step b) is operated and said trap of step b) is a silica gel, activated carbon, activated aluminium oxide and/or molecular sieves working at a temperature ranging from 20 to 100° C. and/or a LHSV between 1 to 10 h-1, and/or a pressure ranging from 1 to 90 barg in presence of H2 or in absence of H2.

7. The method according to claim 1, wherein concerning said hydroprocessing step d) one or more of the following statements is true:

after said hydroprocessing step d), the concentration of olefins as measured via the bromine number in said purified hydrocarbon stream is at most 5.0 gBr2/100 g as measured according to ASTM D1159;

said hydroprocessing step d) is performed in one or more catalyst beds with an overall temperature increase of at most 150° C., and/or a temperature increase of at most 50° C. over each catalyst bed, with intermediary quench between said catalyst beds, said quench being performed with H2 or with said purified hydrocarbon stream recovered at step e);

the inlet temperature is of at least 200° C. and at most 500° C.;

the LHSV is between 1 to 10 h-1;

the pressure ranges from 10 to 90 barg in presence of H2;

said hydroprocessing step d) is performed over a catalyst that comprises at least one metal of group VIB in combination or not with a promotor selected from at least one metal of group VIII and/or VIIIB;

the ratio H2/hydrocarbon ranges from 200 NL/L to 900 NL/L;

on the top of the hydroprocessing step d) a silicon trap is present working at a temperature of at least 230° C. and/or a LHSV between 1 to 10 h-1, and/or a pressure ranging from 10 to 90 barg in presence of H2; and/or said second hydrotreating step is performed over at least one catalyst that presents both (i) an hydrotreating function, namely at least one metal of group VIB in combination or not with a promotor selected from at least one metal of group VIII and/or VIIIB, and/or mixture thereof, these metals being used in sulfided form and (ii) a trap function, namely said catalyst presents a BET surface area ranging from 150 m2/g to 400 m2/g.

8. The method according to claim 1, wherein said pyrolysis plastic is originating directly, i.e. without further treatment or modification, from a waste plastic pyrolyzer where waste plastics been thermally pyrolyzed or alternatively said pyrolysis plastic oil and/or said hydrocarbon stream of step a) is treated before said step b) in one or more of the followed pre-treatment unit:

in a desalting unit to remove water-soluble salts;

in an impurities removal treatment step to remove silicon, phosphorous, metals and/or halogenated compounds, via a solvent extraction or in a guard bed, said guard bed preferably working at a temperature of at most 250° C., and/or a LHSV between 1 to 10 h-1, and/or a pressure ranging from 1 to 90 barg either in presence of H2 or in the absence of H2 in a separation unit to extract the particles and gums by filtration, centrifugation or a combination of the two technics; and/or in a dewatering unit to remove water in said hydrocarbon stream to reach a water content of less than 0.1% vol according to ASTM D95.

9. The method according to claim 1, wherein said process for purification comprises the preliminary step a1) of providing a waste plastic stream; a2) pyrolyzing said waste plastic stream at a temperature of at least 200° C.; a3) recovering a pyrolizer effluent and separating said pyrolizer effluent into a C1 to C4 hydrocarbons fraction, a fraction having a boiling range higher than 350° C. and a fraction being said pyrolysis plastic oil; a4) sending said fraction having a boiling range higher than 350° C. into a FCC, or an hydrocracking unit, a coker or a visbreaker or blending said fraction having a boiling range higher than 350° C. in crude oil or in a crude oil cut to be further refined.

10. The method according to claim 1, wherein the effluent obtained after said hydroprocessing step is further washed with water to remove inorganic compounds further hydrocracked at a temperature of 350-430° C., a pressure of 30-180 barg, a LHSV of 0.5-4 h-1, and/or under H2 to hydrocarbons ratio of 800-2000 NL:L to reduce the final boiling point of at least 10% prior to be sent at least partially to the steam cracker.

11. The method according to claim 1, wherein said first diluent is selected from a naphtha and/or a paraffinic solvent and/or a diesel or a straight run gasoil, containing at most 1 wt % of sulfur, and/or an hydrocarbon stream having a starting boiling point of at least 15° C. and a final boiling point of 560° C., and/or having a bromine number of at most 5 gBr2/100 g, and/or a diene value of at most 0.5 gI2/100 g and/or said first diluent is said purified hydrocarbon stream recovered at step e) or any combination thereof.

12. The method according to claim 1, wherein before the step c) a hydrotreating step b1) is performed at a temperature of at most 225° C., wherein one or more of the following statements is true:

the inlet temperature ranges from 25 to 225° C.;

the LHSV ranges from 1 to 10 h-1;

the pressure ranges from 10 to 90 barg in presence of H2, and/or the molar ratio of H2 to the total molar sum of alkynes and dienes in said hydrocarbon stream is of at least 1.5 to at most 15;

said first hydrotreating step is performed in one or more catalyst bed with an overall temperature increase of at most 150° C., and/or a temperature increase of at most 100° C. for each catalyst bed, with intermediary quench between said catalyst beds, said quench being performed with H2 or with said purified hydrocarbon stream recovered at step f);

said first step is performed in a fixed bed reactor over a catalyst that comprises at least one metal of group VIII on a support selected from the group consisting of alumina, titania, silica, zirconia, magnesia, carbon and/ or mixtures thereof; or said catalyst is a Ni based catalyst being passivated after its reduction using di-alkyl-sulfide such as DiMethylSulfide (DMS) or DiEthylSulfide (DES) or thiophenic compounds;

said first step is performed in a fixed bed reactor over a catalyst that comprises at least one metal of group VIB in combination or not with a promotor selected from at least one metal of group VIII and/VIIIB these metals being used in sulfided form; and/or the effluents obtained at the exit of said first hydrotreating step has a diene value of at most 1.5 g I2/100 g.

13. The method according to claim 1, wherein said second diluent is part of said purified hydrocarbon stream obtained at step e) that is directly recycled at step c) without further heating.

14. The method according to claim 4, wherein at least 10 wt % to at most 80 wt % of said purified hydrocarbon stream recovered at step e) is directly recycled at step c) as said second diluent without further heating.

15. The method according to claim 7, wherein the at least one metal of group VIB is Mo or W, and the at least one metal of group VIII and/or VIIIB is Ni and/or Co.

16. The method according to claim 7, wherein the at least one metal of group VIB and/or the at least one metal of group VIII and/or VIIIB are used in sulfided form and supported on alumina, titania, zirconia, silica, carbon and/or mixtures thereof.

17. The process according to claim 10, wherein the inorganic compound is selected from the group consisting of hydrosulphide, hydrogenchloride, and ammonia.

18. A method for the purification of a hydrocarbon stream comprising the following steps:

a) providing a hydrocarbon stream having a diene value of at least 1.0 g I2/100 g as measured according to UOP 326 and a bromine number of at least 5 g Br2/100 g as measured according to ASTM D 1159 and containing pyrolysis plastic oil, the other part of said hydrocarbon stream being a first diluent or alternatively providing a hydrocarbon stream containing only pyrolysis plastic oil;

b) optionally putting in contact the hydrocarbon stream with silica gel, clays, alkaline or alkaline earth metal oxide, iron oxide, ion exchange resins, active carbon, active aluminium oxide, molecular sieves, alkaline oxide and/or porous supports containing lamellar double hydroxide modified or not and silica gel, or any mixture thereof to trap silicon and/or metals and/or phosphorous and/or halogenates;

c) heating the stream obtained at the step a) or b) at a temperature of at most 230° C. followed by a mixing of the heated stream with a second diluent having a temperature of at least 250° C.;

d) performing an hydroprocessing step at a temperature of at least 230° C. in the presence of H2 on the mixed stream of step c);

e) recovering a purified hydrocarbon stream from the hydroprocessing step, wherein said second diluent is part of said purified hydrocarbon stream obtained at step e) that is directly recycled at step c), and the part of said purified hydrocarbon stream obtained at step e), i.e. the effluent of said hydroprocessing step, having an initial boiling point higher than 200° C. is further sent to a FCC, or an hydrocracking unit, or a coker or a visbreaker or blended in crude oil or base oil or crude oil cut to be further refined.

19. The process according to claim 18, wherein the purified hydrocarbon stream obtained at step e) is sent at least partially and directly to a steam cracker without further dilution and as the only stream sent at least partially to the steam cracker, to produce olefins and aromatics.

\* \* \* \* \*